(12) United States Patent
Russell et al.

(10) Patent No.: US 10,191,052 B2
(45) Date of Patent: Jan. 29, 2019

(54) METHODS OF DIAGNOSING AND TREATING ACTIVE TUBERCULOSIS IN AN INDIVIDUAL

(71) Applicant: ProteinLogic Limited, Cambridge (GB)

(72) Inventors: Roslin Russell, Cambridge (GB); Oliver Stegle, Cambridge (GB); Mahesh Shah, Cambridge (GB)

(73) Assignee: ProteinLogic Limited, Cambridge (GB)

( * ) Notice: Subject to any disclaimer, the term of this patent is extended or adjusted under 35 U.S.C. 154(b) by 160 days.

(21) Appl. No.: 15/115,276

(22) PCT Filed: Jan. 30, 2015

(86) PCT No.: PCT/GB2015/050222
§ 371 (c)(1),
(2) Date: Jul. 29, 2016

(87) PCT Pub. No.: WO2015/114351
PCT Pub. Date: Aug. 6, 2015

(65) Prior Publication Data
US 2017/0003286 A1    Jan. 5, 2017

(30) Foreign Application Priority Data
Jan. 30, 2014   (GB) .................................. 1401603.4

(51) Int. Cl.
G01N 33/569    (2006.01)
(52) U.S. Cl.
CPC ..... *G01N 33/5695* (2013.01); *G01N 2800/52* (2013.01)
(58) Field of Classification Search
CPC ................... G01N 33/5695; G01N 2800/52
See application file for complete search history.

(56) References Cited

U.S. PATENT DOCUMENTS

2011/0196614 A1    8/2011   Banchereau et al.

FOREIGN PATENT DOCUMENTS

| WO | 2003/075016 A1 | 9/2003 |
| WO | 2010/115989 A1 | 10/2010 |

(Continued)

OTHER PUBLICATIONS

U.S. Appl. No. 14/418,502 nonfinal Office Action, dated Feb. 18, 2016, 15 pages.

(Continued)

*Primary Examiner* — Sean C. Barron
(74) *Attorney, Agent, or Firm* — ALGM LLP; Harry J. Guttman

(57) ABSTRACT

The invention relates to biomarkers for diagnosing, monitoring and/or treating *tuberculosis* in both immunocompetent and immunocompromised individuals with or without co-infection with HIV, monitoring the responses of individuals to anti-mycobacterial chemotherapy, monitoring the progression of latent *tuberculosis* to active *tuberculosis*, differentiating active *tuberculosis* from latent *tuberculosis*, and from other clinical conditions that mimic *tuberculosis* (TB). The invention also relates to methods for diagnosing, monitoring and/or treating *tuberculosis* using said biomarkers. The above pertain in all aspects both to pulmonary and extrapulmonary *Mycobacterium tuberculosis* infections, with *Mycobacterium tuberculosis* being the causative organism in *tuberculosis*. The invention therefore finds great utility in assisting with future drug discovery efforts for *tuberculosis* and also provides proxy clinical end points as well as being an effective predictor of a response to treatment.

17 Claims, 24 Drawing Sheets

(56) References Cited

FOREIGN PATENT DOCUMENTS

| | | |
|---|---|---|
| WO | 2012/085652 A2 | 6/2012 |
| WO | 2012167307 A1 | 12/2012 |
| WO | 2013175459 A2 | 11/2013 |
| ZA | 2009/05156 A | 5/2010 |

OTHER PUBLICATIONS

U.S. Appl. No. 14/418,502 Response to nonfinal Office Action, dated Aug. 15, 2016, 49 pages.

U.S. Appl. No. 14/418,502 Notice of Nonresponsive Amendment, dated Nov. 14, 2016, 2 pages.

U.S. Appl. No. 14/418,502 Response to Notice of Nonresponsive Amendment, dated Nov. 16, 2016, 49 pages.

U.S. Appl. No. 14/418,502 final Office Action, dated Apr. 12, 2017, 13 pages.

Abstract from WPI/Thomson of South African Patent No. ZA200905156A, 2 pages.

Benjamani & Hochberg (1995) "Controlling the False Discovery Rate: a Practical and Powerful Approach to Multiple Testing" J. R. Statist. Soc. B (1995) vol. 57, No. 1, pp. 289-300.

Brieman, "Random Forests" Machine Learning (2001) vol. 45 pp. 5-32.

Casrouge et al., "Evidence for an antagonist form of the chemokine CXCL10 in patients chronically infected with HCV" The Journal of Clinical Investigation (2011) vol. 121, No. 1, pp. 308-317.

Chegou et al., "Potential of Host Markers Produced by Infection Phase-Dependent Antigen-Stimulated Cells for the Diagnosis of Tuberculosis in a Highly Endemic Area" PLoS ONE (2012) vol. 7, No. 6, e38501, 10 pages.

Connolly et al., "Hu1nan Siglec-5: tissue distribution, novel isoforms and domain specificities for sialic acid-dependent ligand interactions" British Journal of Haematology (2002) vol. 119, pp. 221-238.

Cornish et al., "Characterization of Siglec-5, a Novel Glycoprotein Expressed on Myeloid Cells Related to CD33" Blood (1998) vol. 92, No. 6, pp. 2123-2132.

Diaz-Uriarte et al, "Gene selection and classification of microarray data using random forest" BMC Bioinformatics (2006) vol. 7, No. 3 (doi:10.1186/1471-2105-7-3) (13 pages).

Dosanjh et al., "Improved Diagnostic Evaluation of Suspected Tuberculosis" Annals of Internal Medicine (2008) vol. 148, No. 5, pp. 325-336.

Fridman et al., "Soluble Fc gamma receptors" Journal of Leukocyte Biology (1993) vol. 54, No. 5, pp. 504-512.

Helwick, "Active TB Infection May Have Unique Cytokine Response Profile" Medscape Medical News—Conference News from American Thoracic Society (ATS) 2010 International Conference, May 14-19, 2010 (2 pages).

Jones et al., "Simultaneous Measurement of Antigen-Stimulated Interleukin-1beta and Gamma Interferon Production Enhances Test Sensitivity for the Detection of *Mycobacterium bovis* Infection in Cattle" Clinical and Vaccine Immunology (2010) vol. 17, No. 12, pp. 1946-1951.

Kellar et al., "Multiple Cytokines Are Released When Blood from Patients with Tuberculosis is Stimulated with *Mycobacterium tuberculosis* Antigens" Plos One (2011) vol. 6, No. 11, article e26545 (doi:10.1371/journal.pone.0026545) (17 pages).

Painter et al., "Tuberculosis Screening by Tuberculosis Skin Test or QuantiFERON®-TB Gold In-Tube Assay among an Immigrant Population with a High Prevalence of Tuberculosis and BCG Vaccination" PLoS ONE (2013) vol. 8, No. 12, article e82727. (doi: 10.1371/journal.pone.0082727) (9 pages).

R&D Systems Proteome Profiler Array Human Soluble Receptor Array Kit Hematopoietic Panel (Product Insert, 2009) (20 pages).

RayBiotech Quantibody Human Cytokine Antibody Array 4000 User Manual (2010) (22 pages).

Robin et al., "pROC: an open-source package for R and S+ to analyze and compare ROC curves" BMC Bioinformatics (2011) vol. 12, No. 77 (DOI: 10.1186/1471-2105-12-77 ) (8 pages).

Rokhlin et al., "Soluble forms of CD44 and CD54 (ICAM-1) cellular adhesion molecules are released by human prostatic cancer cell lines" Cancer Letters (1996) vol. 107, No. 1, pp. 29-35.

Shkarin et al. (2008)—English-language abstract from National Center for Biotechnology Information, www.ncbi.nlm.nih.gov/pubmed/18819336?report=abstract&format=text , 1 page.

Shkarin et al. "Plasma Levels of Cytokines in Patients with Active Infiltrative Pulmonary Tuberculosis" Problemy Tuberkuleza Bolezn. Legk. (2008) vol. 8, pp. 34-38.

Sing et al., "ROCR: visualizing classifier performance in R" Bioinformatics (2005) vol. 21, No. 20, pp. 3940-3941.

Tsiouris et al., "Sensitivity Analysis and Potential Uses of a Novel Gamma Interferon Release Assay for Diagnosis of Tuberculosis" J. Clin. Microbiol. (2006) vol. 44, No. 8, pp. 2844-2850.

Walzl et al., "Immunological biomarkers of tuberculosis" Nature Reviews/Immunology (2011) vol. 11, pp. 343-354.

Wang et al., "Investigation of the effect of *Mycobacterium bovis* infection on bovine neutrophils functions" Tuberculosis (2013) vol. 93, No. 6, pp. 675-687.

Wong et al., "Assay of pleural fluid interleukin-6, tumour necrosis factor-alpha and interferon-gamma in the diagnosis and outcome correlation of tuberculous effusion" Respiratory Medicine (2003) vol. 97, pp. 1289-1295.

Wu et al., "Messenger RNA Expression of IL-8, FOXP3, and IL-12 Beta Differentiates Latent Tuberculosis Infection from Disease" J. Immunol. (2007) vol. 178, pp. 3688-3694.

Zhao et al., "Regulation of Membrane Metalloproteolytic Cleavage of L-selectin (CD62L) by the Epidermal Growth Factor Domain" The Journal of Biological Chemistry (2001) vol. 276, No. 33, pp. 30631-30640.

METHODS OF DIAGNOSING AND TREATING ACTIVE TUBERCULOSIS IN AN INDIVIDUAL

CROSS-REFERENCE TO RELATED APPLICATIONS

This application is a US National Stage Entry of International Application No. PCT/GB2015/050222 filed Jan. 30, 2015, entitled "BIOMARKERS" which is herein incorporated by reference in its entirety, and which claims priority to GB 1401603.4 filed Jan. 30, 2014, entitled "BIOMARKERS" which is herein incorporated by reference in its entirety.

FIELD OF THE INVENTION

The invention relates to biomarkers for diagnosing, monitoring and/or treating *tuberculosis* in both immunocompetent and immunocompromised individuals with or without co-infection with HIV, monitoring the responses of individuals to anti-mycobacterial chemotherapy, monitoring the progression of latent *tuberculosis* to active *tuberculosis*, differenti at ingactive *tuberculosis* from latent *tuberculosis*, and from other clinical conditions that mimic *tuberculosis* (TB). The invention also relates to methods for diagnosing, monitoring and/or treating *tuberculosis* using said biomarkers. The above pertain in all aspects both to pulmonary and extrapulmonary *Mycobacterium tuberculosis* infections, with *Mycobacterium tuberculosis* being the causative organism in *tuberculosis*. The invention therefore finds great utility in assisting with future drug discovery efforts for *tuberculosis* and also provides proxy clinical end points as well as being an effective predictor of a response to treatment.

BACKGROUND OF THE INVENTION

*Mycobacterium tuberculosis* is arguably one of the most successful pathologic micro-organisms worldwide, and is the causative agent of the potentially lethal infectious disease *tuberculosis*. It is also the leading cause of death worldwide from a potentially curable infectious disease, with an estimated two million related deaths annually.

The pathogenesis of TB is complex, with the initial infection occurring as the result of the inhalation of aerosolized infectious *Mycobacterium tuberculosis*. The immunological response to the bacillary insult dictates whether the infected individual will proceed to develop either localized pulmonary disease, latent disease (LTBI) or disseminated disease as a consequence of haematogenous spread. Those acquiring latent disease remain asymptomatic but retain the potential to evolve into active disease (this occurs in approximately 10% of all cases over a lifetime period).

It is estimated that approximately one third of the world's population is infected with either latent or active *tuberculosis*. Recent figures from 2012 report a total of 8751 cases of active *tuberculosis* in the UK. This represents an overall upward trend over the last decade. The number of *Mycobacterium tuberculosisisolates* resistant to antibiotics is also increasing.

Pulmonary TB is the most common clinical presentation of infection with *Mycobacterium tuberculosis*. Symptoms typically include chronic cough with or without haemoptysis, fever, night sweats, and weight loss. Only individuals with active pulmonary disease remain infectious as they have the ability to aerosolize bacilli. Infection of almost any other organ system may occur with diverse accompanying clinical presentations. Immunocompromised individuals may present atypically.

The pathogen has shown a dramatic resurgence, driven in part by the HIV epidemic in sub-Saharan Africa, as the immunological response of these individuals is compromised. This has a two fold impact. Firstly, individuals are more likely to progress from pre-existing latent disease to active disease and secondly, primary infection is more likely to take the form of active disease with increased infectivity. With increasing globalisation, the detection, prevention and early appropriate treatment of this aerosolised pathogen is becoming an increasingly important public health priority.

Despite extensive research, the current understanding of the immunological response and pathogenesis of *Mycobacterium tuberculosis* remains incomplete. Furthermore, the existing diagnostics and treatment methods are suboptimal. *Tuberculosis* is definitively diagnosed by the identification of the causative organism (*Mycobacterium tuberculosis*) in a clinical specimen. This is achieved by prolonged culture of the organism, or by PCR analysis. Adjuncts to definitive diagnosis include: diagnostic imaging (X-rays or radiological scans), tuberculin skin tests (Mantoux/Heaf tests) and Interferon Gamma Release Assays (IGRAs).

Existing barriers to rapid definitive TB diagnosis include the difficulty in culturing this slow-growing organism in the laboratory, which can take around 3 to 12 weeks, or in obtaining an appropriate sample containing Mycobacterial DNA for PCR. The latter may require invasive sampling in the case of extrapulmonary TB, which is costly and may involve additional risks to the patient. Recent developments in the field of TB diagnostics include the Xpert MTB/RIF test which has been endorsed by the World Health Authority This is for use in sputum samples to diagnose cases of suspected active pulmonary *tuberculosis*, and to detect rifampicin resistant mutations, which are a marker for multidrug resistant *tuberculosis*. This methodology is, however, dependent on a PCR-positive sample being obtained.

As a consequence of suboptimal diagnostic tools, anti-microbial combination chemotherapy treatment is often commenced empirically on the basis of clinical suspicion in conjunction with the results of adjunctive diagnostic tests. The rationale for this approach is two fold. The patient receives a therapeutic trial of anti-microbial chemotherapy, and in cases of pulmonary *tuberculosis*, transmission is curtailed through the reduction of the bacillary load in the sputum.

Current diagnostic adjuncts include: radiological imaging, IGRAs and tuberculin skin testing (TST). Imaging provides guidance as to whether typical features are present, whereas IGRAs and TST provide information regarding possible prior exposure to *M. tuberculosis* by interrogating the immunological response to TB-related antigens. Interpretation of both the IGRA and TST tests is complex and confounded by a number of factors. These include amongst several others: prior exposure (latent disease), prior vaccination with BCG, and immunosupression. IGRA has, however, increasingly become an accepted adjunctive tool in countries with a low prevalence of TB for evaluating the likelihood of tuberculous disease being present. Unfortunately imaging, TST and the IGRA test are unable to definitively diagnose the presence of active disease.

Recent publications have emphasized the potential for utilising combinations of biomarkers as diagnostic tools for *tuberculosis*. WO 03/075016 describes that levels of soluble proteins detectable in the blood, namely soluble CD antigens ("sCD") sCD15, sCD23, sCD27 and sCD54, may be altered in patients with *tuberculosis*. A Medscape Medical News article from the American Thoracic Society (ATS) 2010 International Conference indicated that a combination of IL-15 and MCP-1 accurately categorised 84% of subjects as having active or latent *tuberculosis*. Chegou (2$^{nd}$ Global Symposium on IGRAs May-June 2009) describes that combinations of biomarkers are more promising TB diagnostics than individual biomarkers and suggests measurement of EGF, sCD40L, MIP-1β, VEGF, TGF-α or IL-1α as a rapid test for active TB. Wu et al (2007) J Immunol 178, 3688-3694 indicated that IL-8, FOXP3 and IL-12β offer a means of differentiating between latent *Mycobacterium tuberculosis* infection and active *tuberculosis* disease.

As current diagnostic methodologies for TB are suboptimal, so too are the treatment options available for this disease. As a consequence of the intracellular nature of this pathogen, and lack of adequate innovations in the field of TB therapeutics, the basis of TB therapy continues to be combination anti-microbial chemotherapy over a prolonged period of months in the simplest cases. Partial compliance with treatment may though lead to suboptimal therapeutic levels of the antimicrobials, and the micro-evolution of antibiotic resistance mutations. As a result of this, patients may remain infectious for longer durations, and the frequency of transmission is enhanced. The development of these resistance mutations, some of which are unresponsive to all known anti TB medications (multi-resistant), has recently caused heightened concern in India.

There is therefore a significant need to identify more effective and efficient methods for definitively diagnosing both active and latent TB and in particular differentiating active from latent TB.

SUMMARY OF THE INVENTION

According to a first aspect of the invention, there is provided the use of a panel comprising three or more biomarkers selected from: CD14, CD22, CD25, CD27, CD54, CD62L, CD64, CD120b, CD170, IL-1β, IL-6, IL-8, IL-10, IL-12p70, IL-32, CXCL9, CXCL10, TNF alpha and IFN gamma for diagnosingand/or monitoring *tuberculosis*.

According to a further aspect of the invention, there is provided a method of diagnosing and/or monitoring *tuberculosis*, comprising detecting and/or quantifying the biomarkers defined herein in a clinical sample taken from a test subject.

According to a further aspect of the invention, there is provided a method of diagnosing *tuberculosis* in an individual thereto, comprising:
(a) obtaining a test biological sample from an individual;
(b) quantifying the amount of the biomarkers defined herein;
(c) comparing the amounts of the biomarkers in the test biological sample with the amounts present in one or more control samples, such that a difference in the level of the biomarkers in the test biological sample is indicative of a diagnosis of *tuberculosis*.

According to a furthers aspect of the invention, there is provided a method of monitoring the efficacy of anti-microbial therapy in a subject having or suspected of having *tuberculosis*, comprising detecting and/or quantifying the biomarkers defined herein in a sample from said subject.

According to a further aspect of the invention, there is provided a method of determining the efficacy of anti-microbial therapy for *tuberculosis* in an individual subject comprising:

(a) obtaining a biological sample from an individual;
(b) quantifying the amount of the biomarkers defined herein;
(c) comparing the amounts of the biomarkers in the test biological sample with the amounts present in one or more control samples, such that a difference in the level of the biomarkers in the test biological sample is indicative of a response to the treatment.

According to a further aspect of the invention, there is provided a method of treating *tuberculosis* in an individual in need thereof, wherein said method comprises the following steps:
(a) diagnosing *tuberculosis* in an individual according to the methods described herein; followed by
(b) administering an anti-*tuberculosis* medicament to said individual in the event of a positive diagnosis for *tuberculosis*.

According to a further aspect of the invention, there is provided a method of treating *tuberculosis* in an individual in need thereof, which comprises the step of administering an anti-*tuberculosis* medicament to a patient identified as having differing levels of the biomarkers as defined herein when compared to the levels of said biomarkers from a control subject.

A further aspect of the invention provides ligands, such as naturally occurring or chemically synthesised compounds, capable of specific binding to the biomarker. A ligand according to the invention may comprise a peptide, an antibody or a fragment thereof, or an aptamer or oligonucleotide, capable of specific binding to the biomarker. The antibody can be a monoclonal antibody or a fragment thereof capable of specific binding to the biomarker. A ligand according to the invention may be labelled with a detectable marker, such as a luminescent, fluorescent or radioactive marker; alternatively or additionally a ligand according to the invention may be labelled with an affinity tag, e.g. a biotin, avidin, streptavidin or His (e.g. hexa-His) tag.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or any other natural or artificial chemical entity capable of recognizing the biomarkers, or the use of a biosensor of the invention, or an array of the invention, or a kit of the invention to detect and/or quantify the biomarker. In these uses, the detection and/or quantification can be performed on a biological sample such as from the group consisting of whole blood, serum, plasma, tissue fluid, cerebrospinal fluid (CSF), synovial fluid, follicular fluid, seminal fluid, amniotic fluid, milk, urine, pleural fluid, ascites, bronchoalveolar lavage, saliva, sputum, tears, perspiration, lymphatic fluid, aspirate, bone marrow aspirate and mucus, or an extract or purification therefrom, or dilution thereof.

Diagnostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

A further aspect of the invention is a kit comprising a biosensor capable of detecting and/or quantifying one or more of the biomarkers as defined herein for use in monitoring, diagnosing and/or treating *tuberculosis*.

Biomarkers for *tuberculosis* are essential targets for the discovery of novel targets and drug molecules that reduce or prevent the progression of symptoms associated with the disorder. As the level of the biomarker is indicative of a diagnosis of the disorder and of the likelihood of a drug response, the biomarker is useful for the identification of novel therapeutic compounds in in vitro and/or in vivo assays. The biomarkers outlined in the invention may be employed in methods for screening for compounds that modulate the activity of the biomarker.

Thus, in a further aspect of the invention, there is provided the use of a ligand, as described, which can be a peptide, antibody or fragment thereof or aptamer or oligonucleotide according to the invention, or any other natural or artificial chemical entity capable of recognizing the biomarkers; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the biomarker in a subject, comprising administering a test substance to a subject animal and detecting and/or quantifying the level of the biomarker present in a test sample from the subject.

DETAILED DESCRIPTION OF THE INVENTION

Figure 1:
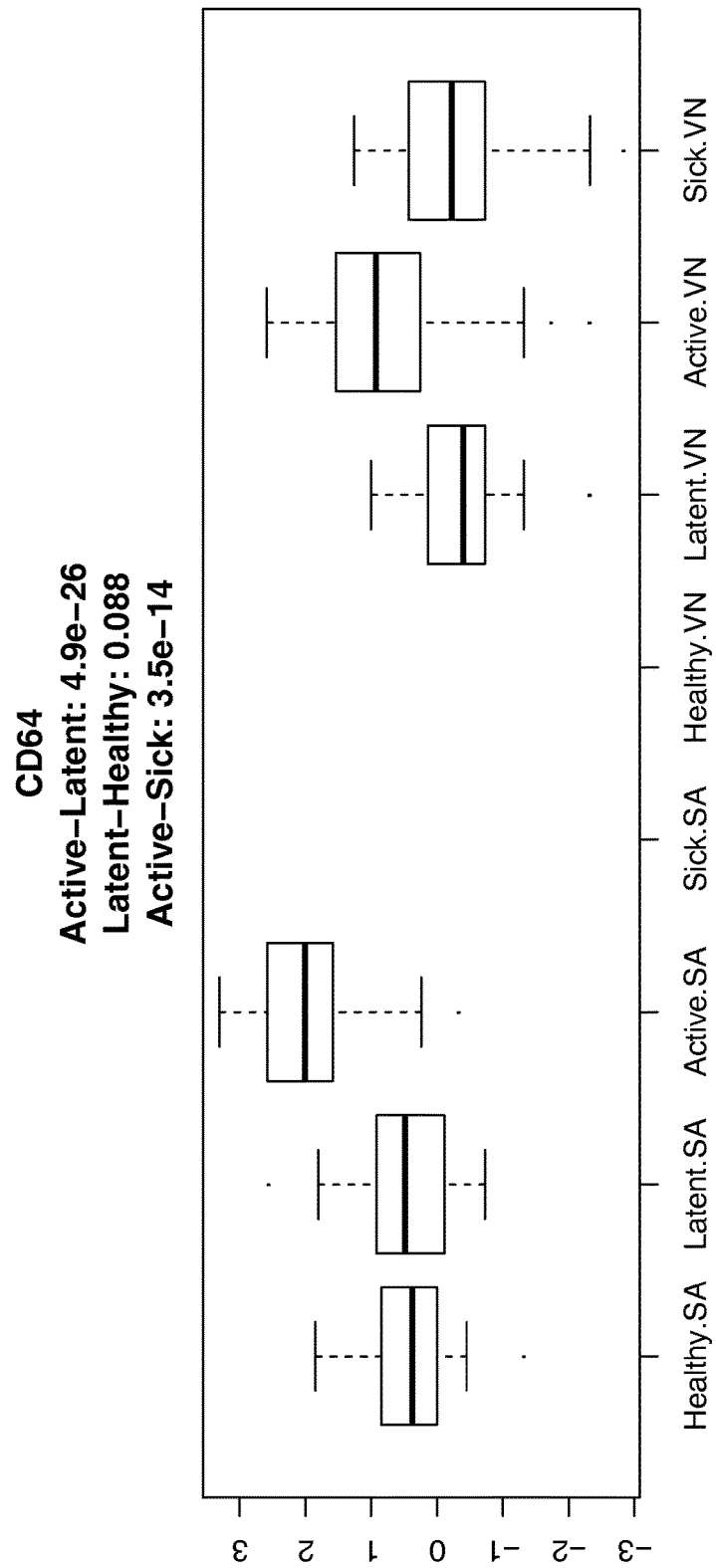
FIG. 1: Example box plot showing means and standard deviations of the analysed result for CD64, the biomarker with the most statistically significant p-value for Active vs. Sick. P-values for active-latent, latent-healthy and active-sick discrimination are shown for this biomarker.

According to a first aspect of the invention, there is provided the use of a panel comprising three or more biomarkers selected from: CD14, CD22, CD25, CD27, CD54, CD62L, CD64, CD120b, CD170, IL-1β, IL-6, IL-8, IL-10, IL-12p70, IL-32, CXCL9, CXCL10, TNF alpha and IFN gamma for diagnosing and/or monitoring *tuberculosis*.

According to a second aspect of the invention, there is provided the use of one or more biomarkers selected from: CXCL10, CD64, CD62L and CD54 for diagnosing and/or monitoring *tuberculosis*.

Data is presented herein in Table 3 which describes the effectiveness of the markers of this aspect of the invention in representing highly sensitive and specific differential diagnostic markers indicative of the diagnosis of key discriminations, such as the ability to differentiate between active and latent *tuberculosis*, latent *tuberculosis* and healthy individuals and active *tuberculosis* and symptomatic non-*tuberculosis* individuals.

In one embodiment, diagnosing and/or monitoring *tuberculosis* comprises diagnosing the presence of or monitoring the response to therapeutic intervention of *tuberculosis*.

In one embodiment, the biomarker comprises CXCL10. References herein to "CXCL10" refer to C-X-C motif chemokine 10 (CXCL10) also known as Interferon gamma-induced protein 10 (IP-10) or small-inducible cytokine B10. CXCL10 is an 8.7 kDa protein that in humans is encoded by the CXCL10 gene. CXCL10 is a small cytokine belonging to the CXC chemokine family.

It will be appreciated that CXCL10 may be used in the invention in either its native form or its soluble form (i.e. antagonist form). A discussion of these differing forms of CXCL10 is described in Casrouge et al (2011) The Journal of Clinical Investigation 121(1), 308-317 where it is hypothesised that dipeptidyl peptidase IV (DPP4; also known as CD26), possibly in combination with other proteases, mediates the generation of the antagonist form(s) of CXCL10.

Data is presented herein in Table 3 which describes the effectiveness of CXCL10 in representing a highly sensitive and specific differential diagnostic marker indicative of the diagnosis of key discriminations, such as the ability to differentiate between active and latent *tuberculosis*, latent *tuberculosis* and healthy individuals and active *tuberculosis* and symptomatic non-*tuberculosis* individuals. Furthermore, the data presented herein in Table 4 demonstrates that CXCL10 provided the single best AUC result for differentiating between active (smear negative) *tuberculosis* and active (smear positive) *tuberculosis*.

In one embodiment, the biomarker comprises CD64. References herein to "CD64" refer to Cluster of Differentiation 64 which is a type of integral membrane glycoprotein known as an Fc receptor that binds monomeric IgG-type antibodies with high affinity. It is more commonly known as Fc-gamma receptor 1 (FcγRI). After binding IgG, CD64 interacts with an accessory chain known as the common γ chain (γ chain), which possesses an ITAM motif that is necessary for triggering cellular activatio. Structurally CD64 is composed of a signal peptide that allows its transport to the surface of a cell, three extracellular immunoglobulin domains of the C2-type that it uses to bind antibody, a hydrophobic transmembrane domain, and a short cytoplasmic tail. CD64 is constitutively found on only macrophages and monocytes, but treatment of polymorphonuclear leukocytes with cytokines like IFNγ and G-CSF can induce CD64 expression on these cells. There are three distinct (but highly similar) genes in humans for CD64 called FcγRIA (CD64A), FcγRIB (CD64B), and FcγRIC (CD64C) that are located on chromosome 1. These three genes produce six different mRNA transcripts; two from CD64A, three from CD64B, and one from CD64C; by alternate splicing of the genes.

Figure 2:
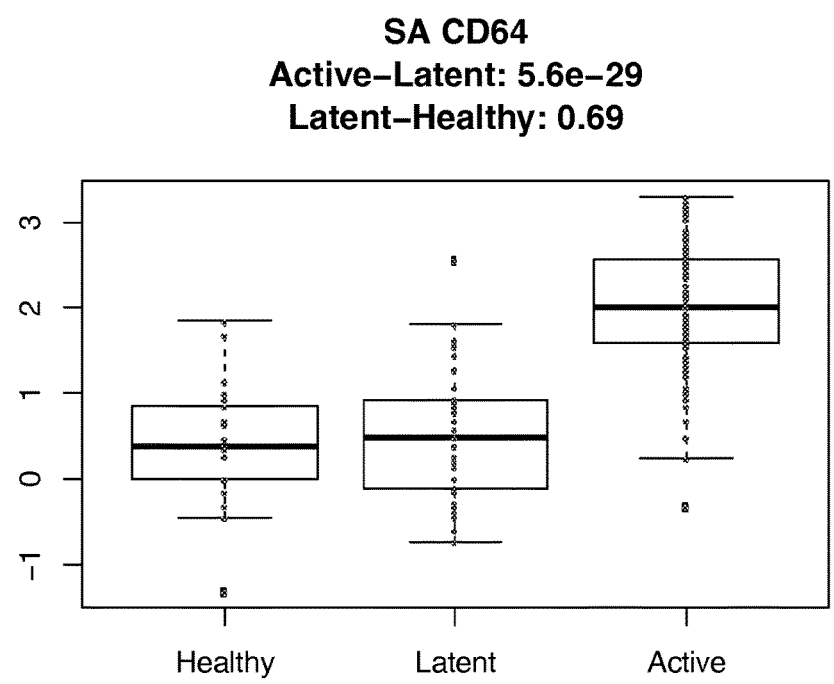
FIG. 2: Example box plot showing means and standard deviations of the analysed result for CD64, the biomarker with the most statistically significant p-value for Active vs. Sick, for Vietnam samples only. P-values for active-latent and active-sick discrimination are shown for this biomarker based on Vietnam cohort of samples only.
Figure 3:
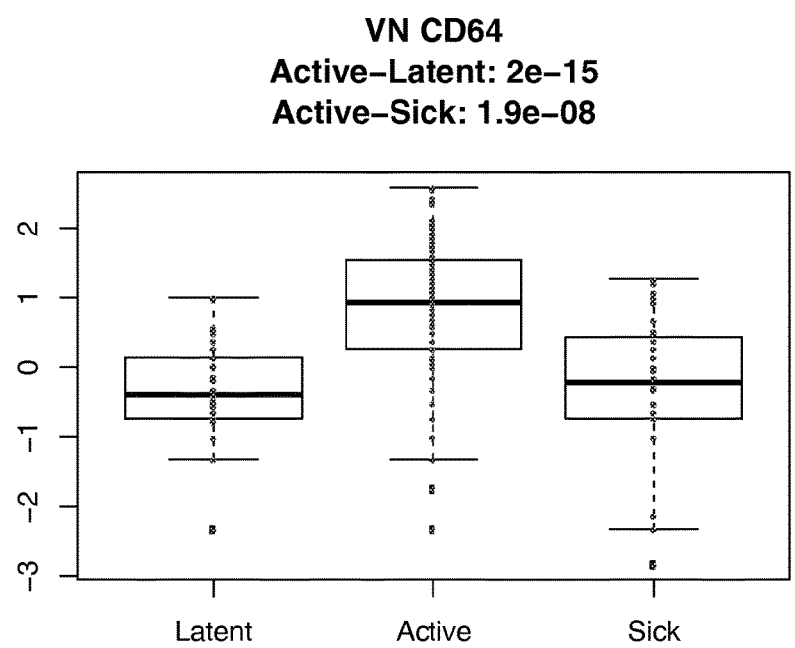
FIG. 3: Example box plot showing means and standard deviations of the analysed result for CD64, the biomarker with the most statistically significant p-value for Active vs. Sick, for South African samples only. P-values for active-latent and latent-healthy discrimination are shown for this biomarker based on South African cohort of samples only.
Figure 4:
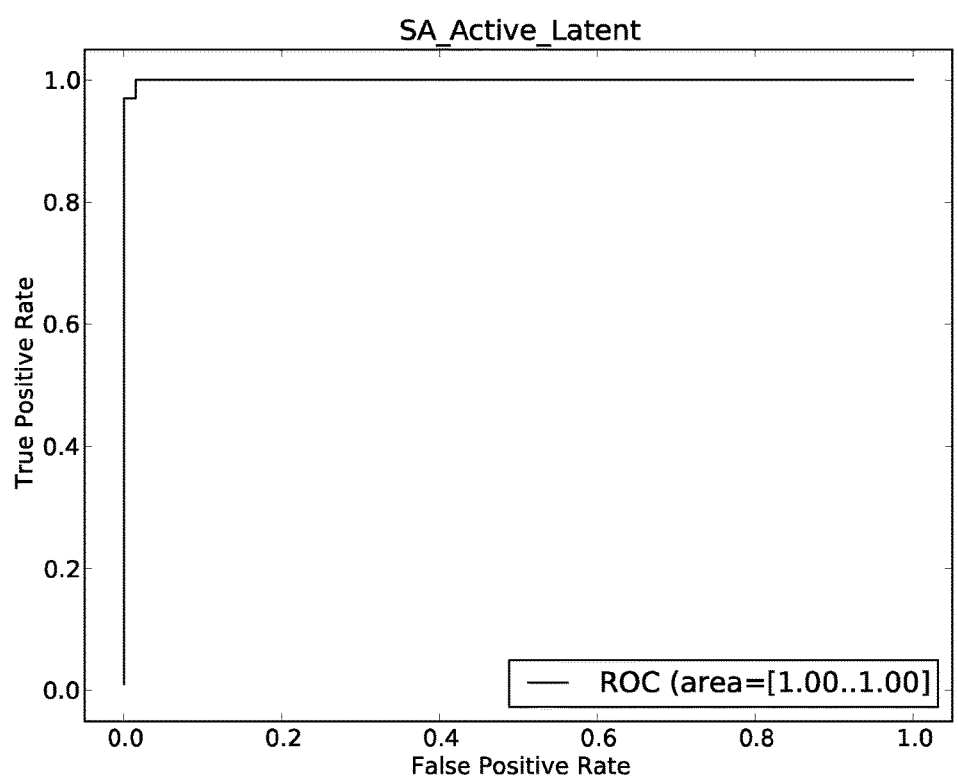
FIG. 4: Example ROC curve based on prediction of South African active TB and South African latent TB from combination of biomarker expressions (this example uses the complete 15 biomarker set). The training set is comprised of South African active TB and South African latent.
Figure 5:
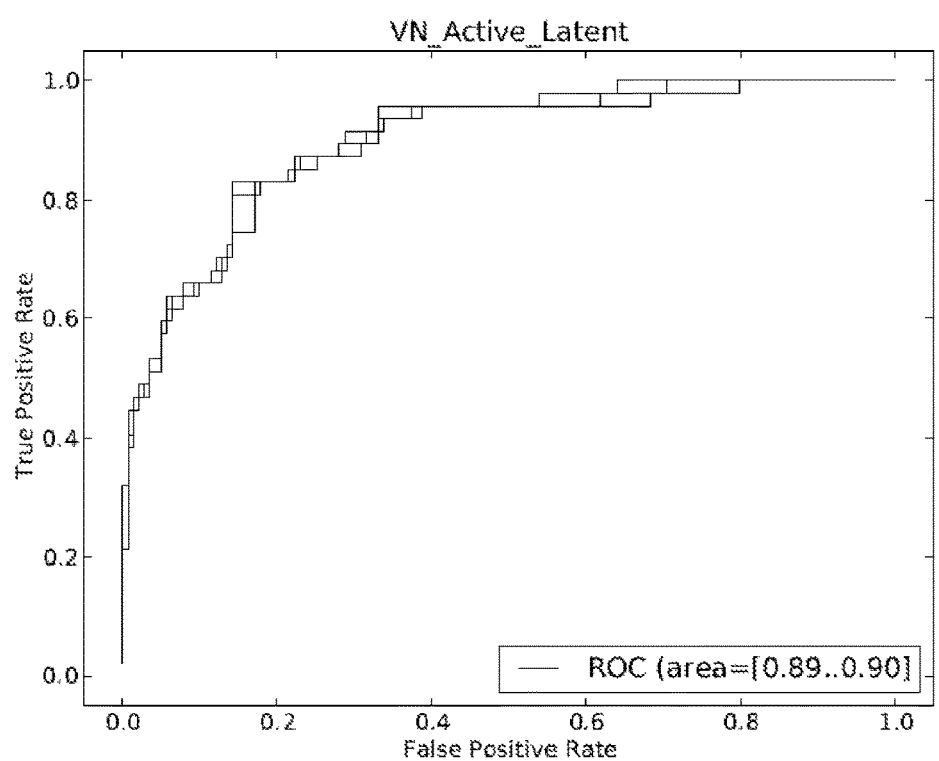
FIG. 5: Example ROC curve based on prediction of Vietnam active TB and Vietnam latent TB from combination of biomarker expressions (this example uses the complete 15 biomarker set). The training set is comprised of Vietnam active TB and Vietnam latent.
Figure 6:
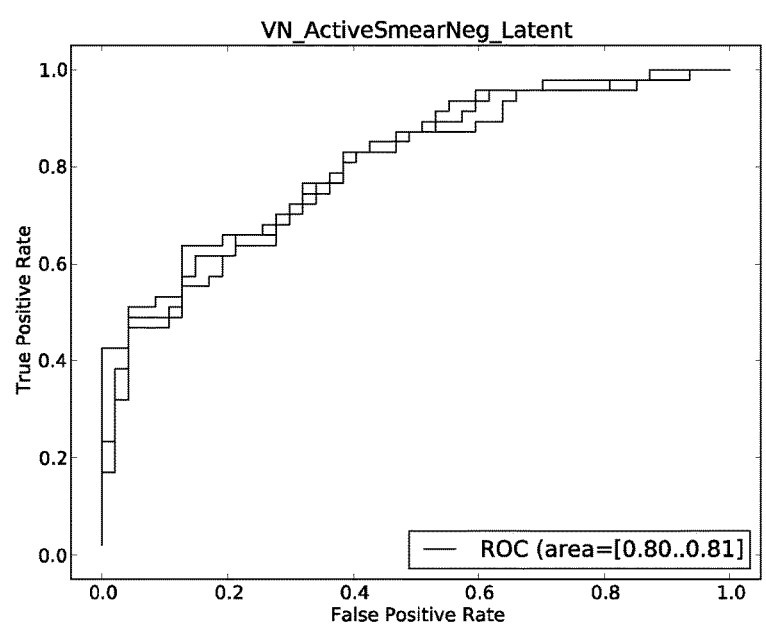
FIG. 6: Example ROC curve based on prediction of Vietnam active TB with negative smear test only and Vietnam latent TB from combination of biomarker expressions (this example uses the complete 15 biomarker set). The training set is comprised of Vietnam active TB with negative smear test only and Vietnam latent.
Figure 7:
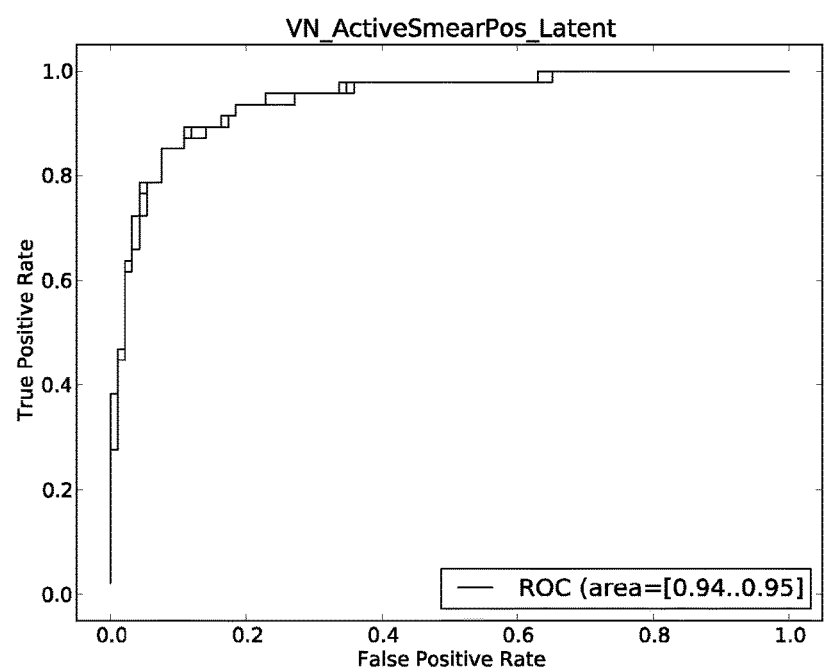
FIG. 7: Example ROC curve based on prediction of Vietnam active TB with positive smear test only and Vietnam latent TB from combination of biomarker expressions (this example uses the complete 15 biomarker set). The training set is comprised of Vietnam active TB with positive smear test only and Vietnam latent.
Figure 8:
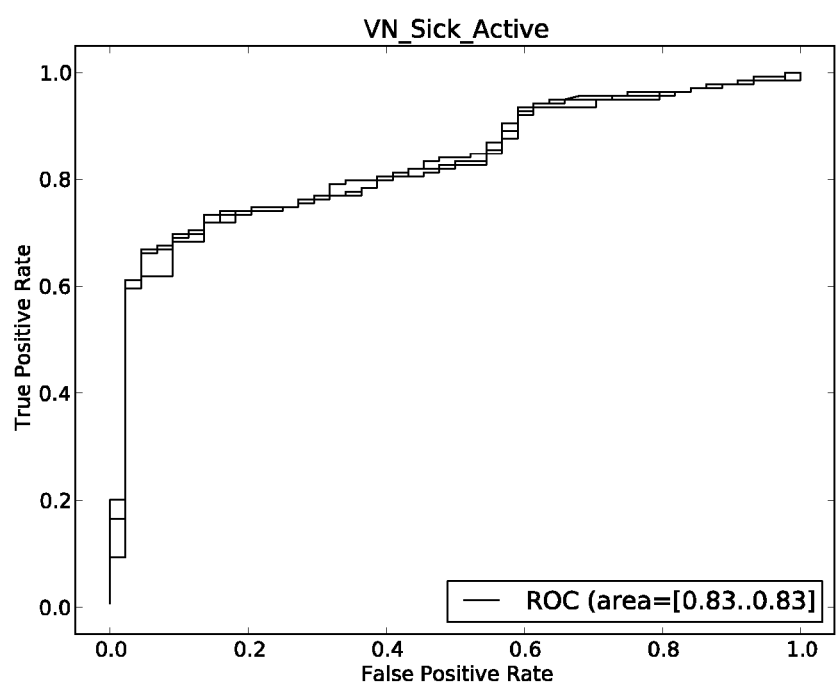
FIG. 8: Example ROC curve based on prediction of Vietnam active TB and Vietnam sick (non-TB) from combination of biomarker expressions (this example uses the complete 15 biomarker set). The training set is comprised of Vietnam active TB and Vietnam sick (non-TB).
Figure 9:
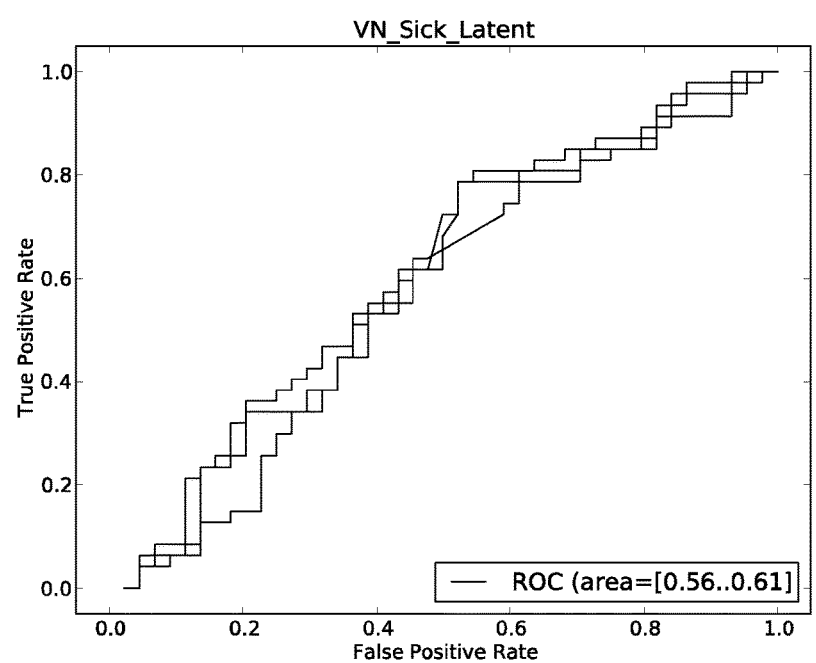
FIG. 9: Example ROC curve based on prediction of Vietnam latent TB and Vietnam sick (non-TB) from combination of biomarker expressions (this example uses the complete 15 biomarker set). The training set is comprised of Vietnam latent TB and Vietnam sick (non-TB).
Figure 10:
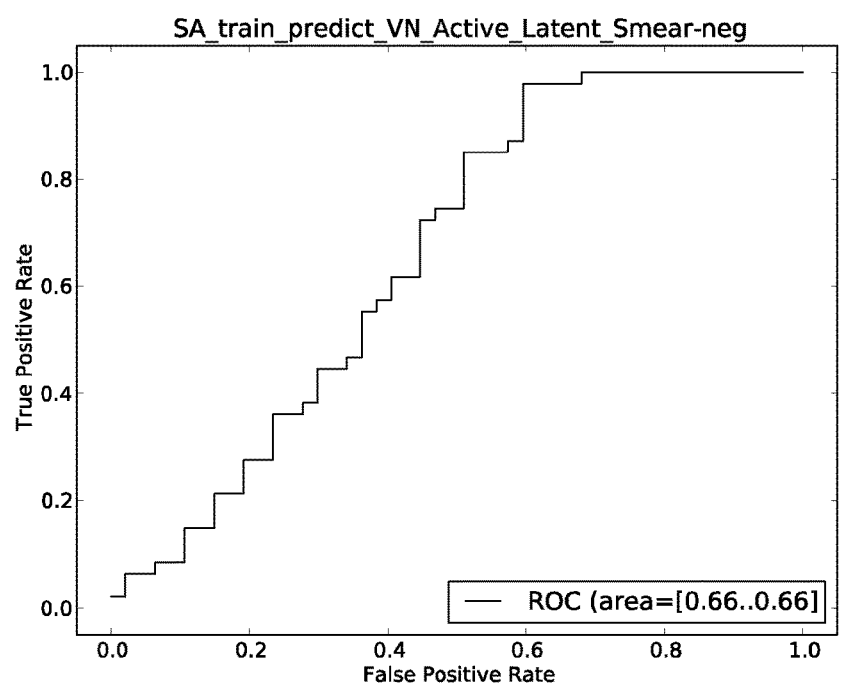
FIG. 10: Example ROC curve based on prediction of Vietnam active TB with negative smear test only and Vietnam latent TB from combination of biomarker expressions (this example uses the complete 15 biomarker set). The training set is comprised of South African active TB (all South African samples were smear positive) and South African latent.
Figure 11:
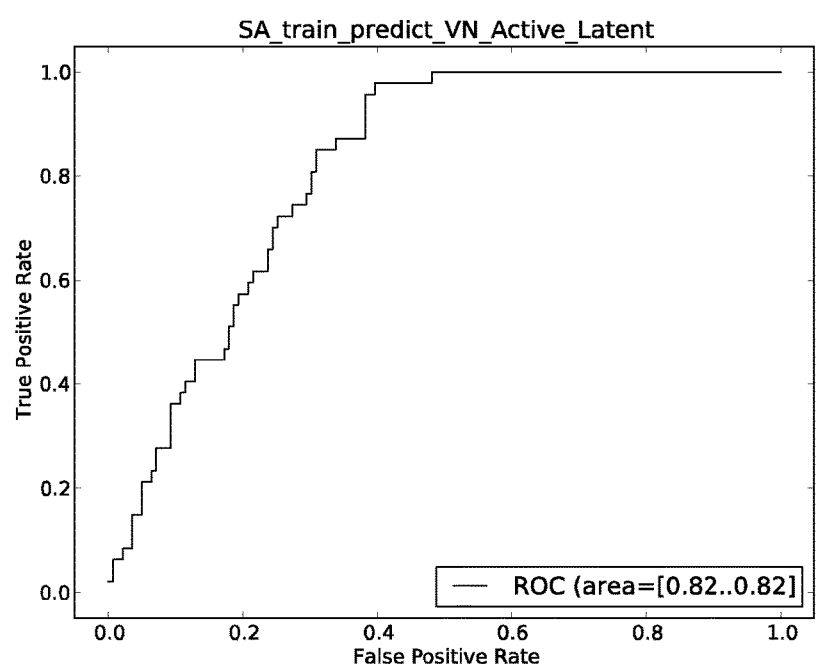
FIG. 11: Example ROC curve based on prediction of Vietnam active TB and Vietnam latent TB from combination of biomarker expressions (this example uses the complete 15 biomarker set). The training set is comprised of South African active TB (all South African samples were smear positive) and South African latent.
Figure 12:
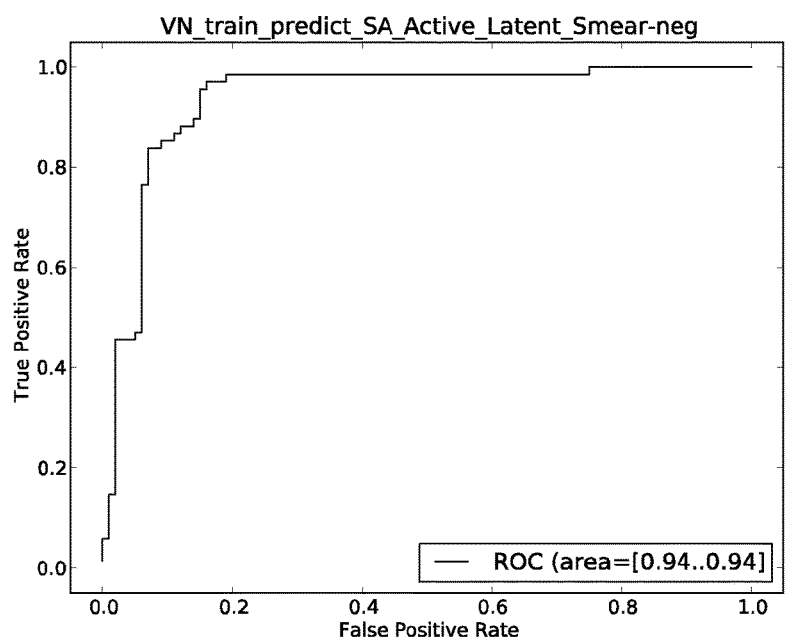
FIG. 12: Example ROC curve based on prediction of South African active TB (all South African samples were smear positive) and South African latent from combination of biomarker expressions (this example uses the complete 15 biomarker set). The training set is comprised of Vietnam active TB with negative smear test only and Vietnam latent TB.
Figure 13:
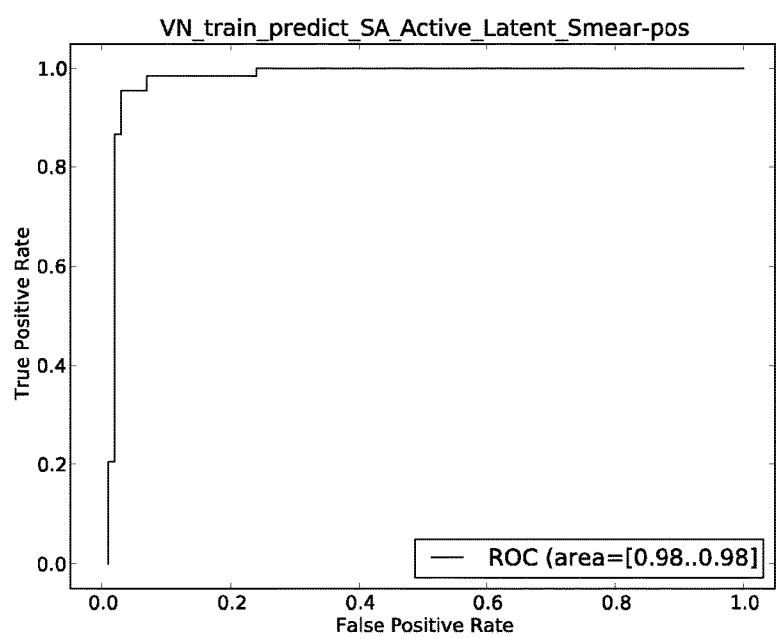
FIG. 13: Example ROC curve based on prediction of South African active TB (all South African samples were smear positive) and South African latent from combination of biomarker expressions (this example uses the complete 15 biomarker set). The training set is comprised of Vietnam active TB with positive smear test only and Vietnam latent TB.
Figure 14:
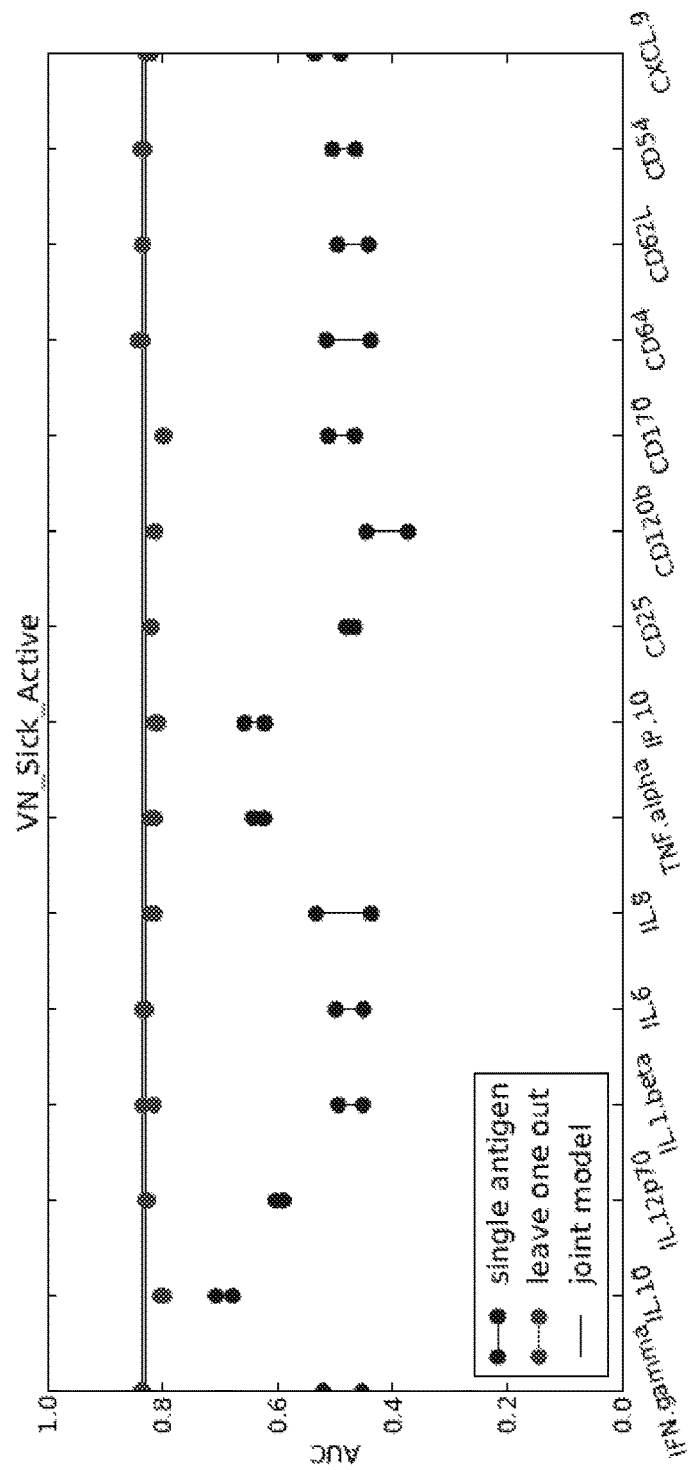
FIG. 14: Example diagram showing the AUC for prediction for individual biomarkers and for the whole panel (IFN gamma, IL-10, IL-12 p70, IL-1β, IL-6, IL-8, TNF alpha, CXCL10, CD25, CD120b, CD170, CD64, CD62L, CD54 and CXCL9) with the one biomarker removed. The AUCs are for ROC curves based on prediction of Vietnam active TB and Vietnam sick (non-TB) from combination of biomarker expressions (this example uses the complete 15 biomarker set). The training set is comprised of Vietnam active TB and Vietnam sick (non-TB).
Figure 15:
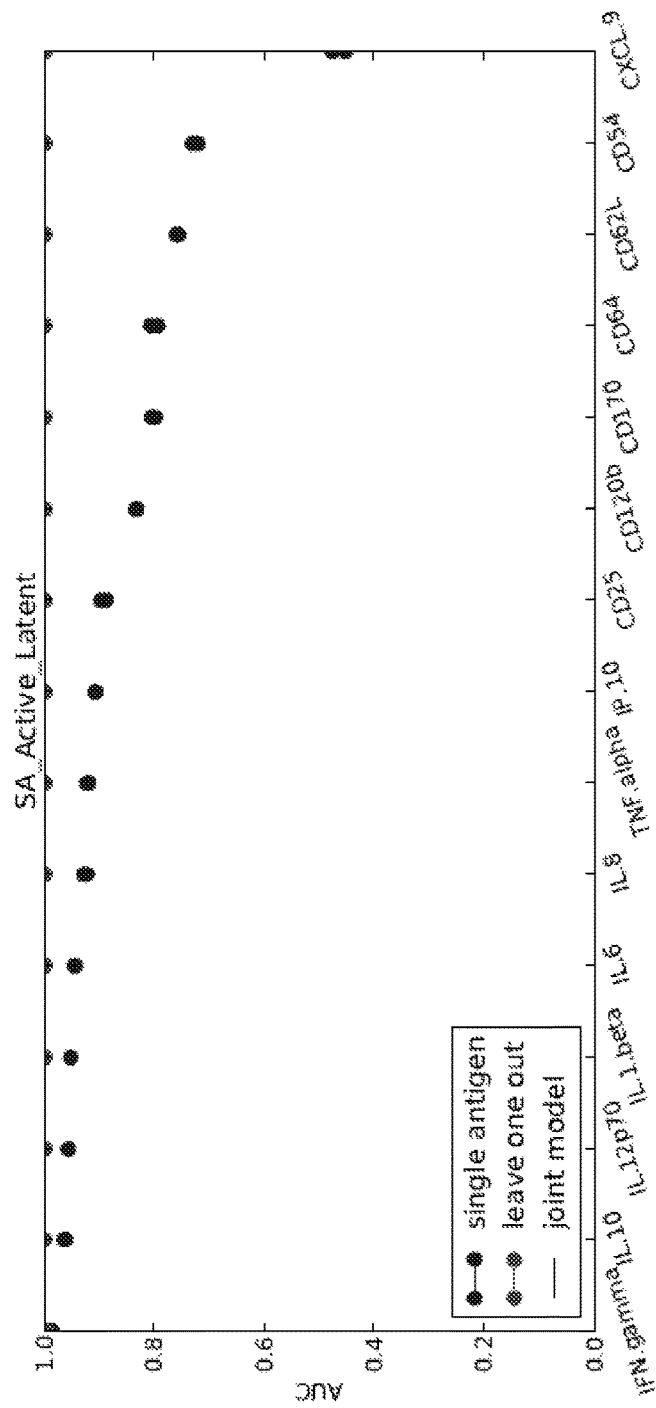
FIG. 15: Example diagram showing the AUC for prediction for individual biomarkers and for the whole panel (IFN gamma, IL-10, IL-12 p70, IL-1β, IL-6, IL-8, TNF alpha, CXCL10, CD25, CD120b, CD170, CD64, CD62L, CD54 and CXCL9) with the one biomarker removed. The AUCs are for ROC curves based on prediction of South African active TB and South African latent TB from combination of biomarker expressions (this example uses the complete 15 biomarker set). The training set is comprised of South African active TB and South African latent TB.
Figure 16:
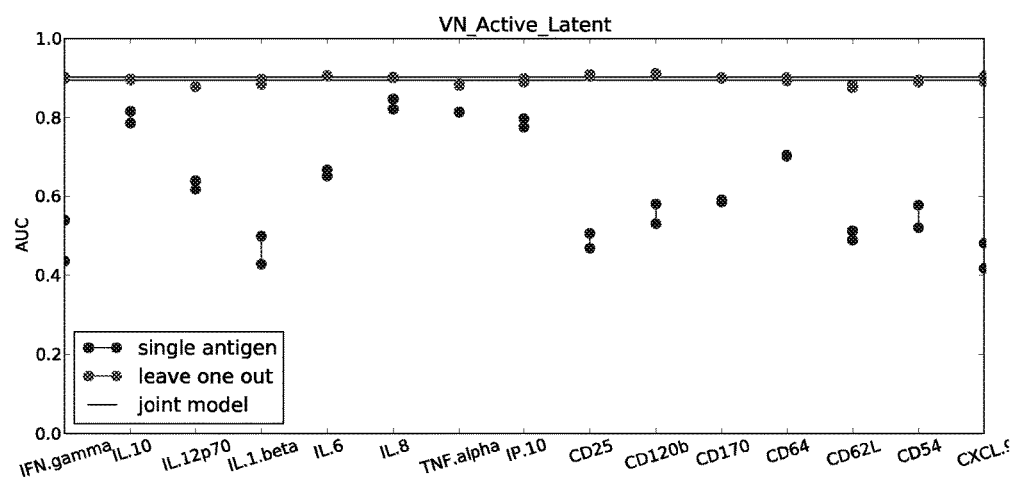
FIG. 16: Example diagram showing the AUC for prediction for individual biomarkers and for the whole panel (IFN gamma, IL-10, IL-12 p70, IL-1β, IL-6, IL-8, TNF alpha, CXCL10, CD25, CD120b, CD170, CD64, CD62L, CD54 and CXCL9) with the one biomarker removed. The AUCs are for ROC curves based on prediction of Vietnam active TB and Vietnam latent TB from combination of biomarker expressions (this example uses the complete 15 biomarker set). The training set is comprised of Vietnam active TB and Vietnam latent TB.

It will be appreciated that CD64 may be used in the invention in either its membrane associated form or its soluble form (i.e. sCD64). A discussion of these differing forms of Fcγ is described in Fridman et al (1993) Journal of Leukocyte Biology 54, 504-512 where it is hypothesised that soluble Fcγ receptors are produced either by alternative splicing of the exon encoding the transmembrane region of the receptor or by proteolytic cleavage at the cell membrane. In one embodiment, the biomarker comprises sCD64. In a further embodiment, the biomarker comprises sCD64A (i.e. FcγRIA). Data is presented herein in Table 3 which describes the effectiveness of sCD64A in representing a highly sensitive and specific differential diagnostic marker indicative of the diagnosis of key discriminations, such as the ability to differentiate between active and latent *tuberculosis*, latent *tuberculosis* and healthy individuals and active *tuberculosis* and symptomatic non-*tuberculosis* individuals. In particular, it can be seen from Table 3 that CD64 demonstrated the most statistically significant p-value for Active vs. Symptomatic non-*tuberculosis* individuals. Data for CD64 is also shown in FIGS. 1-3. Furthermore, the data presented herein in Table 4 demonstrates that CD64 provided the single best AUC result for differentiating between active (smear positive) *tuberculosis* and symptomatic non-*tuberculosis* individuals.

In one embodiment, the biomarker comprises CD62L. References herein to "CD62L" refer to Cluster of Differentiation 62L (also known as L-selectin or SELL), is a cell adhesion molecule found on lymphocytes and the preimplantation embryo. It belongs to the selectin family of proteins, which recognize sialylated carbohydrate groups. It is cleaved by ADAM17. CD62L is a cell surface component that is a member of a family of adhesion/homing receptors that play important roles in lymphocyte-endothelial cell interactions. The molecule is composed of multiple domains: one homologous to lectins, one to epidermal growth factor, and two to the consensus repeat units found in C3/C4-binding proteins.

It will be appreciated that CD62L may be used in the invention in either its membrane associated form or its soluble form (i.e. sCD62L). A discussion of these differing forms of CD62L is described in Zhao et al (2001) The Journal of Biological Chemistry 276(33), 30631-30640 where it is hypothesised that soluble CD62L is produced by rapid cleavage from the surface of activated leukocytes by TNF alpha converting enzyme, a cell surface metalloprotease, and also undergoes slower constitutive shedding in unactivated cells. In one embodiment, the biomarker comprises sCD62L. Data is presented herein in Table 3 which describes the effectiveness of sCD62L in representing a highly sensitive and specific differential diagnostic marker indicative of the diagnosis of key discriminations, such as the ability to differentiate between active and latent *tuberculosis*, latent *tuberculosis* and healthy individuals and active *tuberculosis* and symptomatic non-*tuberculosis* individuals. Furthermore, the data presented herein in Table 4 demonstrates that CD62L provided the single best AUC result for differentiating between active (smear negative) *tuberculosis* and symptomatic non-*tuberculosis* individuals.

In one embodiment, the biomarker comprises CD54. References herein to "CD54" refer to Cluster of Differentiation 54 (also known as ICAM-1; Intercellular Adhesion Molecule 1). CD54 is a protein that in humans is encoded by the ICAM1 gene. This gene encodes a cell surface glycoprotein which is typically expressed on endothelial cells and cells of the immune system. It binds to integrins of type CD11a/CD18, or CD11b/CD18 and is also exploited by rhinovirus as a receptor.

It will be appreciated that CD54 may be used in the invention in either its membrane associated form or its soluble form (i.e. sCD54). A discussion of these differing forms of CD54 is described in Rokhlin and Cohen (1996) Cancer Letters 107, 29-35 where it is hypothesised that release of soluble CD54 is caused by alternative splicing. In one embodiment, the biomarker comprises sCD54. Data is presented herein in Table 3 which describes the effectiveness of sCD54 in representing a highly sensitive and specific differential diagnostic marker indicative of the diagnosis of key discriminations, such as the ability to differentiate between active and latent *tuberculosis*, latent *tuberculosis* and healthy individuals and active *tuberculosis* and symptomatic non-*tuberculosis* individuals.

In one embodiment of any of the aforementioned aspects of the invention, the biomarkers are selected from two or more of: CXCL10, CD64, CD62L and CD54.

In one embodiment of any of the aforementioned aspects of the invention, the biomarkers are selected from three or more of: CXCL10, CD64, CD62L and CD54.

In one embodiment of any of the aforementioned aspects of the invention, all four of: CXCL10, CD64, CD62L and CD54 are selected as biomarkers. Thus, according to a further aspect of the invention, there is provided the use of each of: CXCL10, CD64, CD62L and CD54 as a specific panel of biomarkers for diagnosing and/or monitoring *tuberculosis*.

In one embodiment, the diagnosis comprises the differential diagnosis of any one of: active *tuberculosis* and latent *tuberculosis*; active (smear positive) *tuberculosis* and latent *tuberculosis*; active (smear negative) *tuberculosis* and latent *tuberculosis*; active *tuberculosis* and healthy control(s); latent *tuberculosis* and healthy control(s); active *tuberculosis* and sick control(s); active (smear negative) *tuberculosis* and sick control(s); active (smear positive) *tuberculosis* and sick control(s); latent *tuberculosis* and sick control(s) and active *tuberculosis*, HIV positive and active *tuberculosis*, HIV negative. In a further embodiment, the diagnosis comprises the differential diagnosis of active *tuberculosis* and latent *tuberculosis*.

Figure 17:
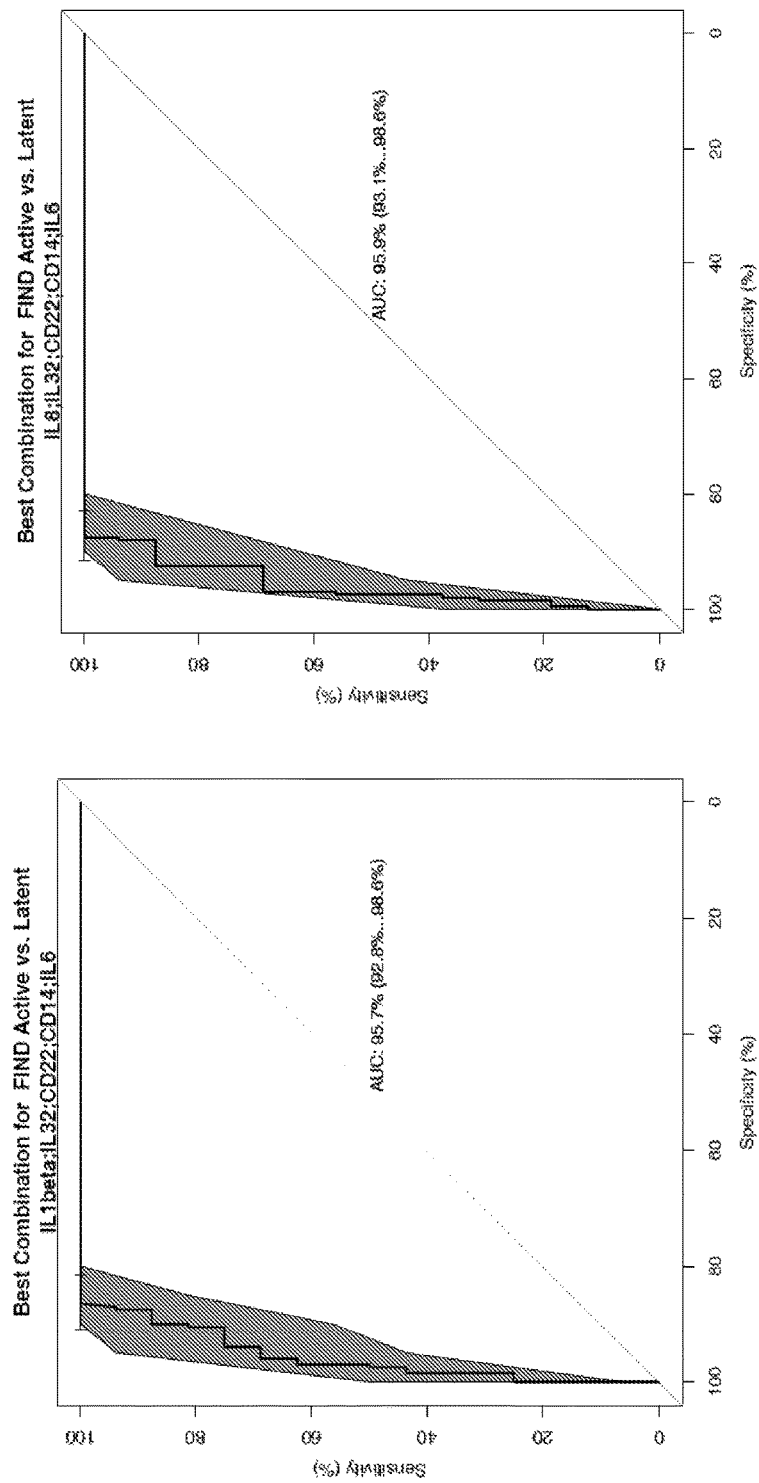
FIG. 17: Two example curves generated from Random Forest classification between samples from Active TB versus Latent TB to identify the best combinations of biomarkers for differentiation between these groups.

In one embodiment, the diagnosis comprises differential diagnosis between active *tuberculosis* and latent *tuberculosis*. In a further embodiment, the diagnosis comprises differential diagnosis between active *tuberculosis* and latent *tuberculosis* and the biomarkers are selected from three or more of: IL-1β, IL-32, CD22, CD14, IL-6 and IL-8. Data is presented in FIG. 17 which shows that these biomarkers were present in the two best combinations tested. In a further embodiment, the diagnosis comprises differential diagnosis between active *tuberculosis* and latent *tuberculosis* and the biomarkers are selected from three or more of: IL-32, CD22, CD14 and IL-6. Data is presented in FIG. 17 which shows that these biomarkers were present in both of the best combinations tested.

Figure 18:
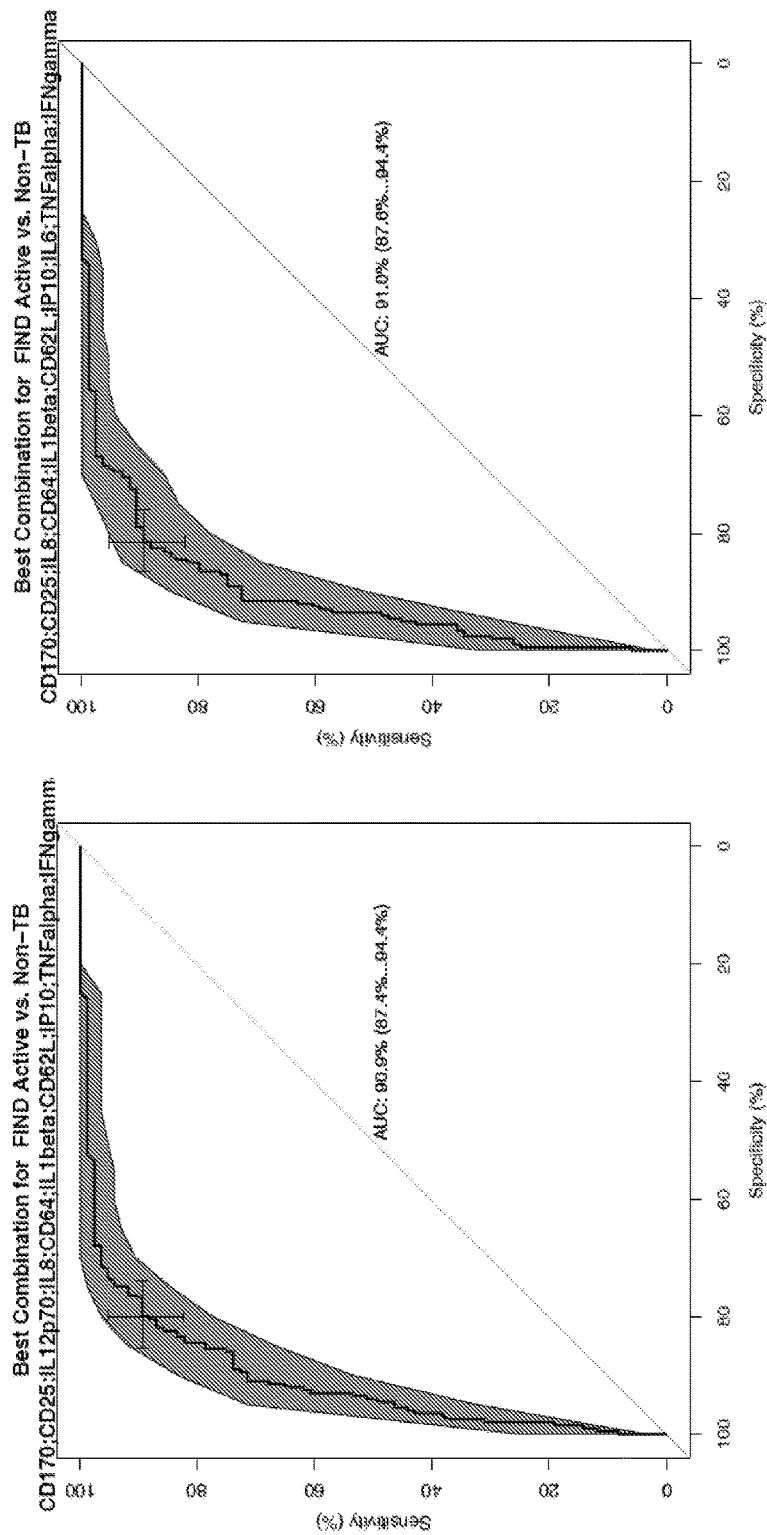
FIG. 18: Two example curves generated from Random Forest classification between samples from Active TB versus Symptomatic Non-TB (Sick) to identify the best combinations of biomarkers for differentiation between these groups.

In one embodiment the diagnosis comprises differential diagnosis between active *tuberculosis* and sick control(s). In a further embodiment, the diagnosis comprises differential diagnosis between active *tuberculosis* and sick control(s) and the biomarkers are selected from three or more of: CD170, CD25, IL-12p70, IL-8, CD64, IL-113, CD62L, CXCL10, TNF alpha, IFN gamma and IL-6. Data is presented in FIG. 18 which shows that these biomarkers were present in the two best combinations tested. In a yet further embodiment, the diagnosis comprises differential diagnosis between active *tuberculosis* and sick control(s) and the biomarkers are selected from three or more of: CD170, CD25, IL-8, CD64, IL-113, CD62L, CXCL10, TNF alpha and IFN gamma. Data is presented in FIG. 18 which shows that these biomarkers were present in both of the best combinations tested.

Figure 19:
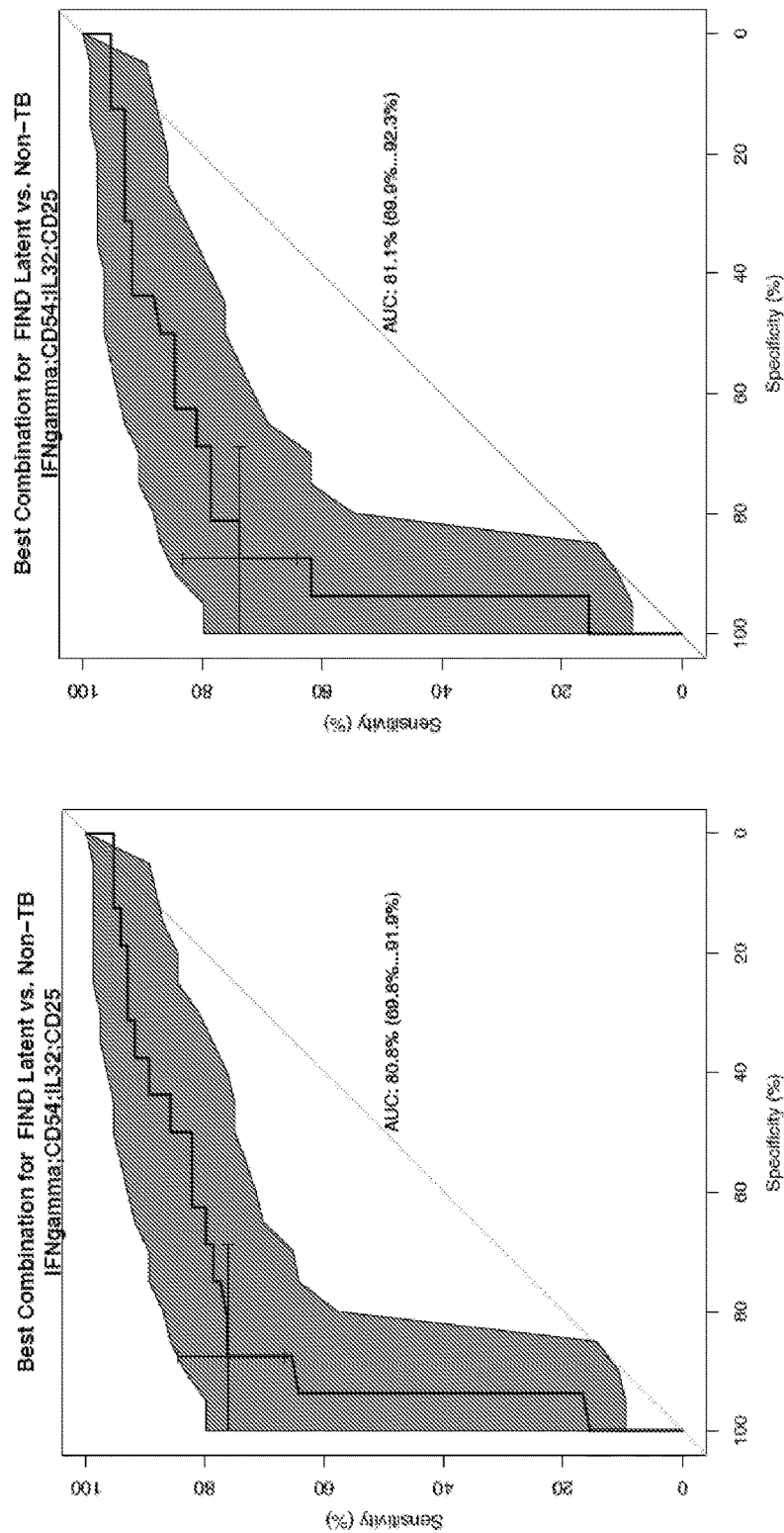
FIG. 19: Two example curves generated from Random Forest classification between samples from Latent TB versus Symptomatic Non-TB (Sick) to identify the best combinations of biomarkers for differentiation between these groups.

In one embodiment, the diagnosis comprises differential diagnosis between latent *tuberculosis* and sick control(s). In a further embodiment, the diagnosis comprises differential diagnosis between latent *tuberculosis* and sick control(s) and the biomarkers are selected from three or more of: IFN gamma, CD54, IL-32 and CD25. Data is presented in FIG. 19 which shows that these biomarkers were present in the two best combinations tested.

Figure 20:
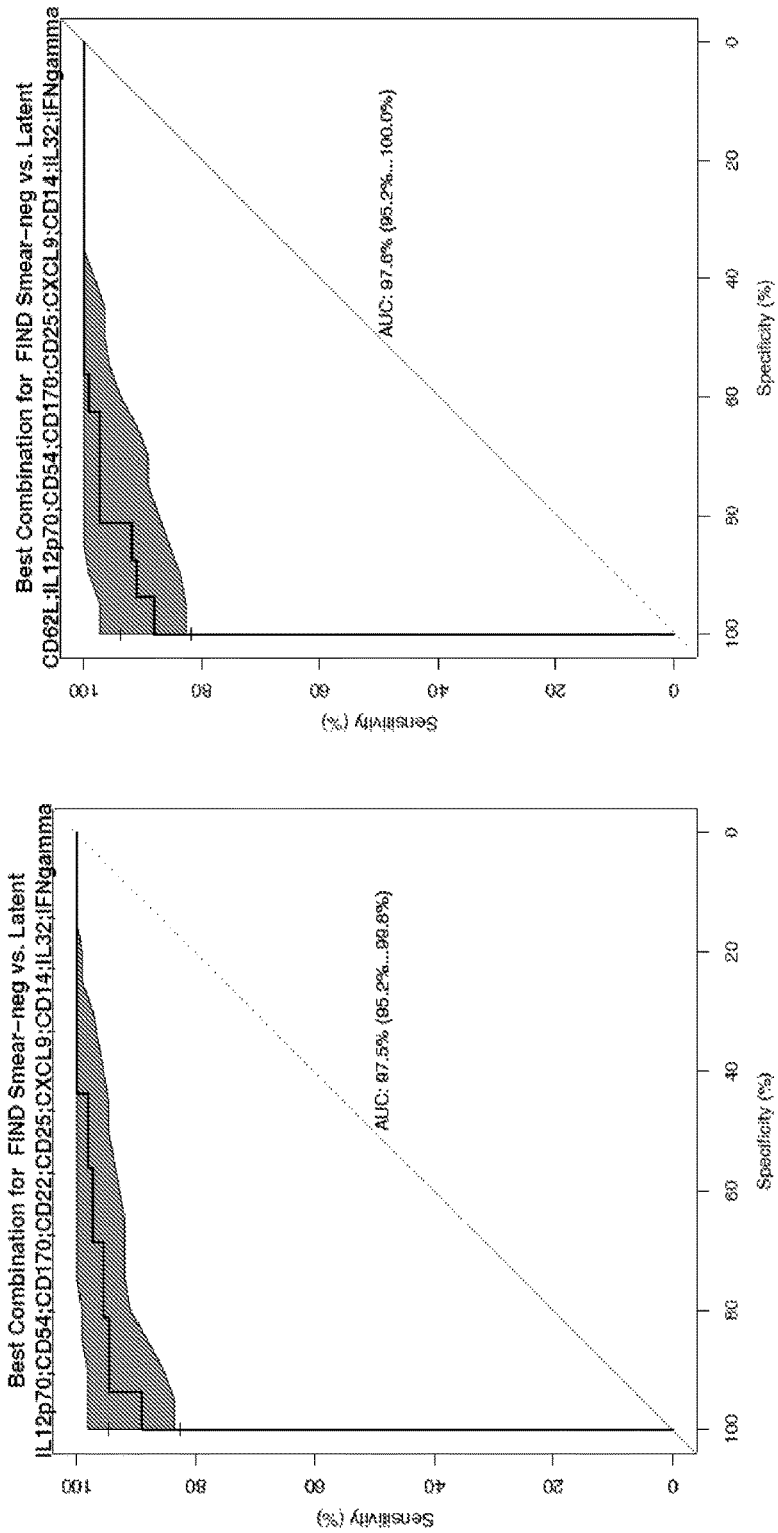
FIG. 20: Two example curves generated from Random Forest classification between samples from Active TB (Smear Neg) versus Latent TB to identify the best combinations of biomarkers for differentiation between these groups.

In one embodiment, the diagnosis comprises differential diagnosis between active (smear negative) *tuberculosis* and latent *tuberculosis*. In a further embodiment, the diagnosis comprises differential diagnosis between active (smear negative)*tuberculosis* and latent *tuberculosis* and the biomarkers are selected from three or more of: IL-12p70, CD54, CD170, CD22, CD25, CXCL9, CD14, IL-32, IFN gamma and CD62L. Data is presented in FIG. 20 which shows that these biomarkers were present in the two best combinations tested.

In a yet further embodiment, the diagnosis comprises differential diagnosis between active (smear negative) *tuberculosis* and latent *tuberculosis* and the biomarkers are selected from three or more of: IL-12p70, CD54, CD170, CD25, CXCL9, CD14, IL-32 and IFN gamma. Data is presented in FIG. 20 which shows that these biomarkers were present in both of the best combinations tested.

Figure 21:
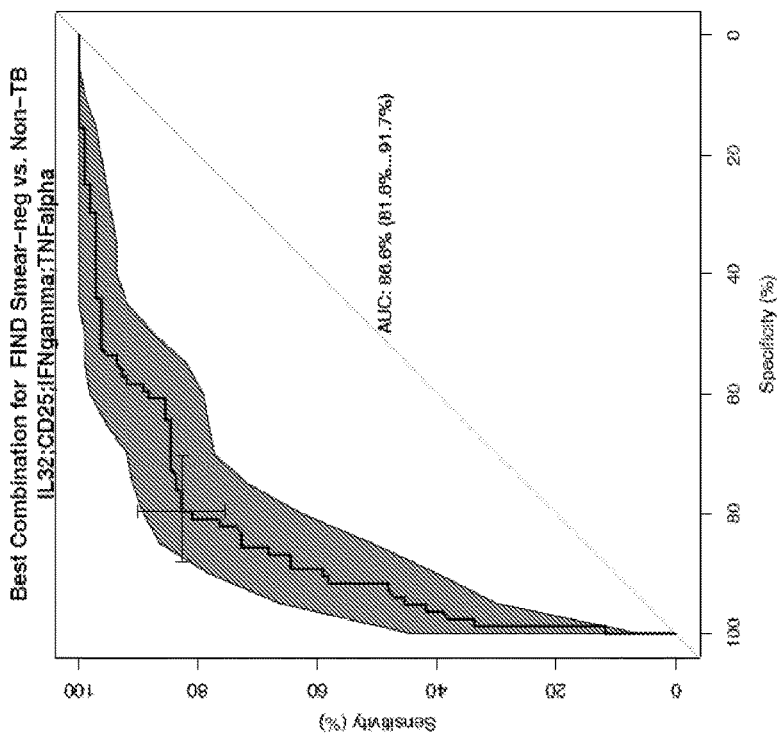
FIG. 21: Two example curves generated from Random Forest classification between samples from Active TB (Smear Neg) versus Symptomatic Non-TB (Sick) to identify the best combinations of biomarkers for differentiation between these groups.
Figure 21:
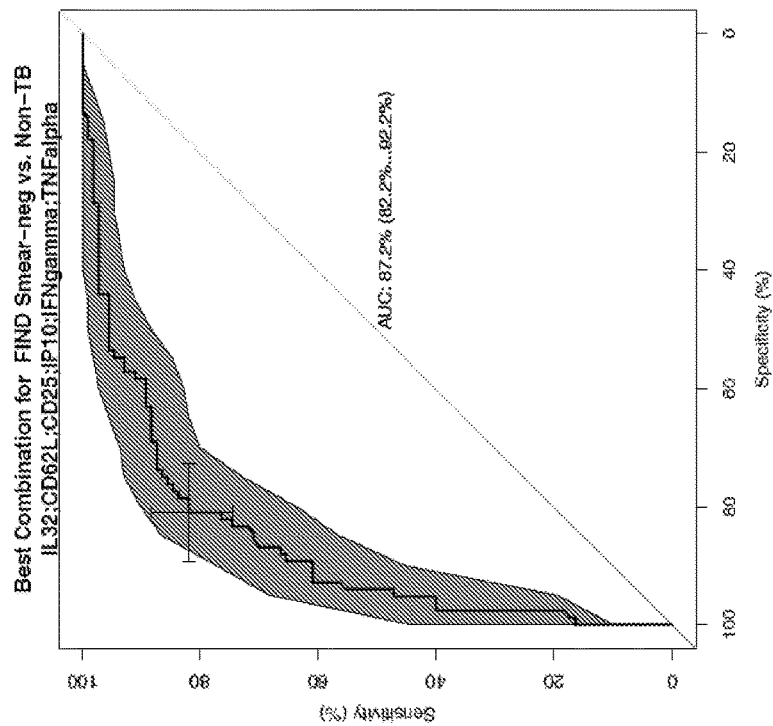

In one embodiment, the diagnosis comprises differential diagnosis between active (smear negative) *tuberculosis* and sick control(s). In a further embodiment, the diagnosis comprises differential diagnosis between active (smear negative) *tuberculosis* and sick control(s) and the biomarkers are selected from three or more of: IL-32, CD62L, CD25, CXCL10, IFN gamma and TNF alpha. Data is presented in FIG. 21 which shows that these biomarkers were present in the two best combinations tested. In a further embodiment, the diagnosis comprises differential diagnosis between active (smear negative) *tuberculosis* and sick control(s) and the biomarkers are selected from three or more of: IL-32, CD25, IFN gamma and TNF alpha. Data is presented in FIG. 21 which shows that these biomarkers were present in both of the best combinations tested.

Figure 22:
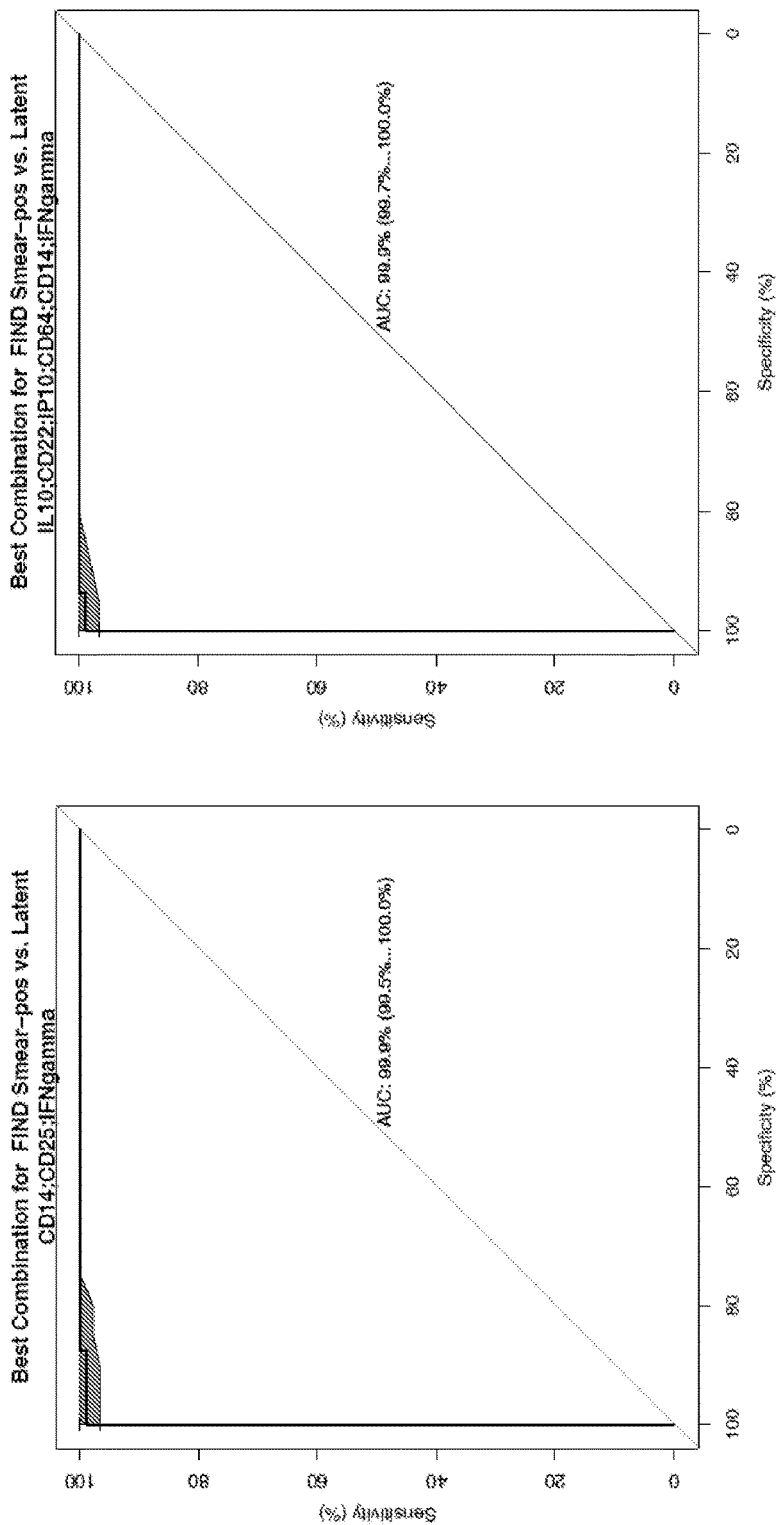
FIG. 22: Two example curves generated from Random Forest classification between samples from Active TB (Smear Pos) versus Latent TB to identify the best combinations of biomarkers for differentiation between these groups.

In one embodiment, the diagnosis comprises differential diagnosis between active (smear positive) *tuberculosis* and latent *tuberculosis*. In a further embodiment, the diagnosis comprises differential diagnosis between active (smear positive) *tuberculosis* and latent *tuberculosis* and the biomarkers are selected from three or more of: CD14, CD25, IFN gamma, IL-10, CD22, CXCL10 and CD64. Data is presented in FIG. 22 which shows that these biomarkers were present in both of the best combinations tested.

Figure 23:
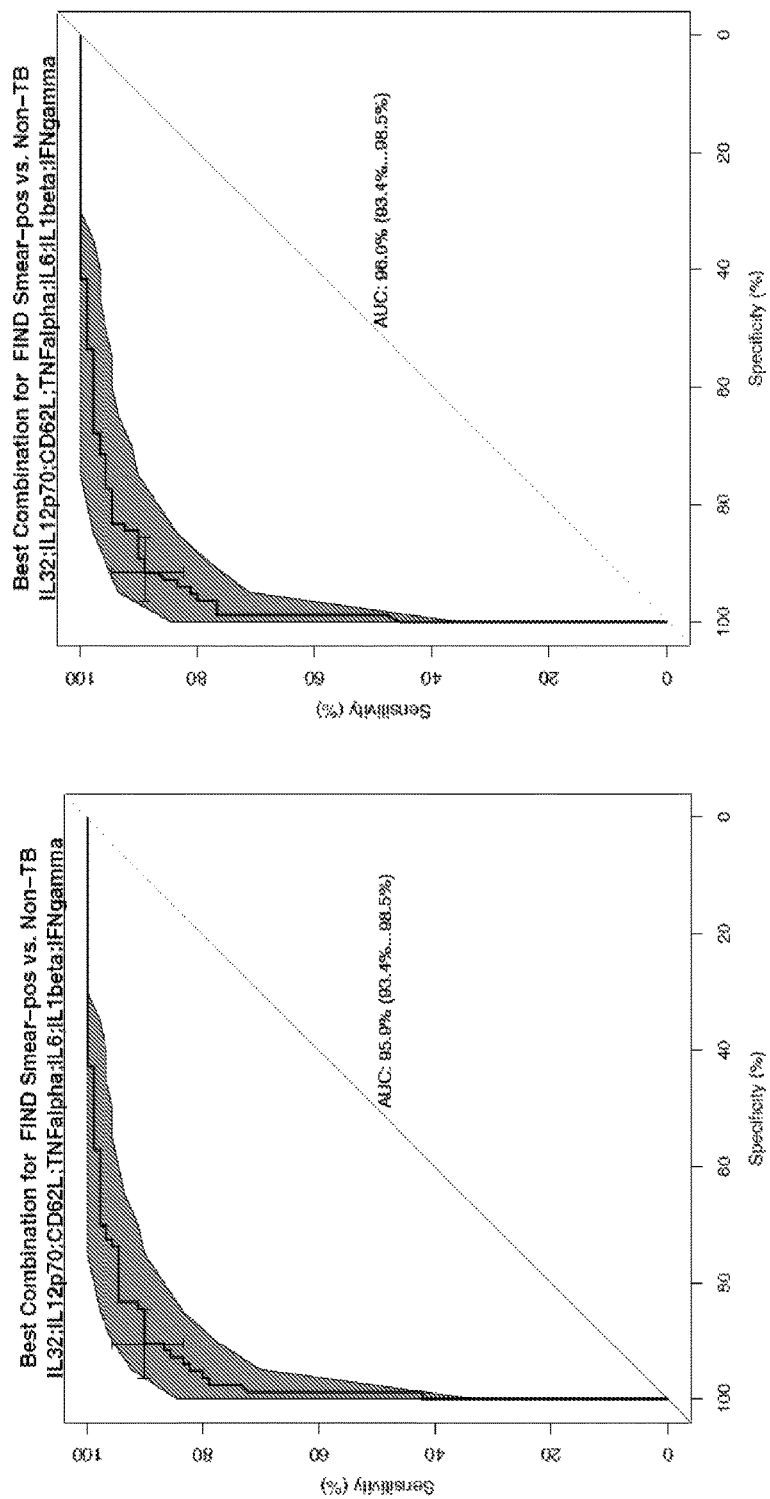
FIG. 23: Two example curves generated from Random Forest classification between samples from Active TB (Smear Pos) versus Symptomatic Non-TB (Sick) to identify the best combinations of biomarkers for differentiation between these groups.

In one embodiment, the diagnosis comprises differential diagnosis between active (smear positive) *tuberculosis* and sick control(s). In a further embodiment, the diagnosis comprises differential diagnosis between active (smear positive) *tuberculosis* and sick control(s) and the biomarkers are selected from three or more of: IL-32, IL-12p70, CD62L, TNF alpha, IL-6, IL-1β and IFN gamma. Data is presented in FIG. 23 which shows that these biomarkers were present in both of the best combinations tested.

In one embodiment, the diagnosis comprises differential diagnosis between active *tuberculosis*, HIV positive and active *tuberculosis*, HIV negative. In a further embodiment, the diagnosis comprises differential diagnosis between active *tuberculosis*, HIV positive and active *tuberculosis*, HIV negative and the biomarkers are selected from three or more of: CD22, CD62L, IL-1β, IL-10, CD14, CD25, IL-32 and CD120b. Data is presented in FIG. 24 which shows that these biomarkers were present in the two best combinations tested. In a yet further embodiment, the diagnosis comprises differential diagnosis between active *tuberculosis*, HIV positive and active *tuberculosis*, HIV negative and the biomarkers are selected from three or more of: IL-1β, IL-10, CD14, CD25, IL-32 and CD120b. Data is presented in FIG. 24 which shows that these biomarkers were present in both of the best combinations tested.

Figure 24:
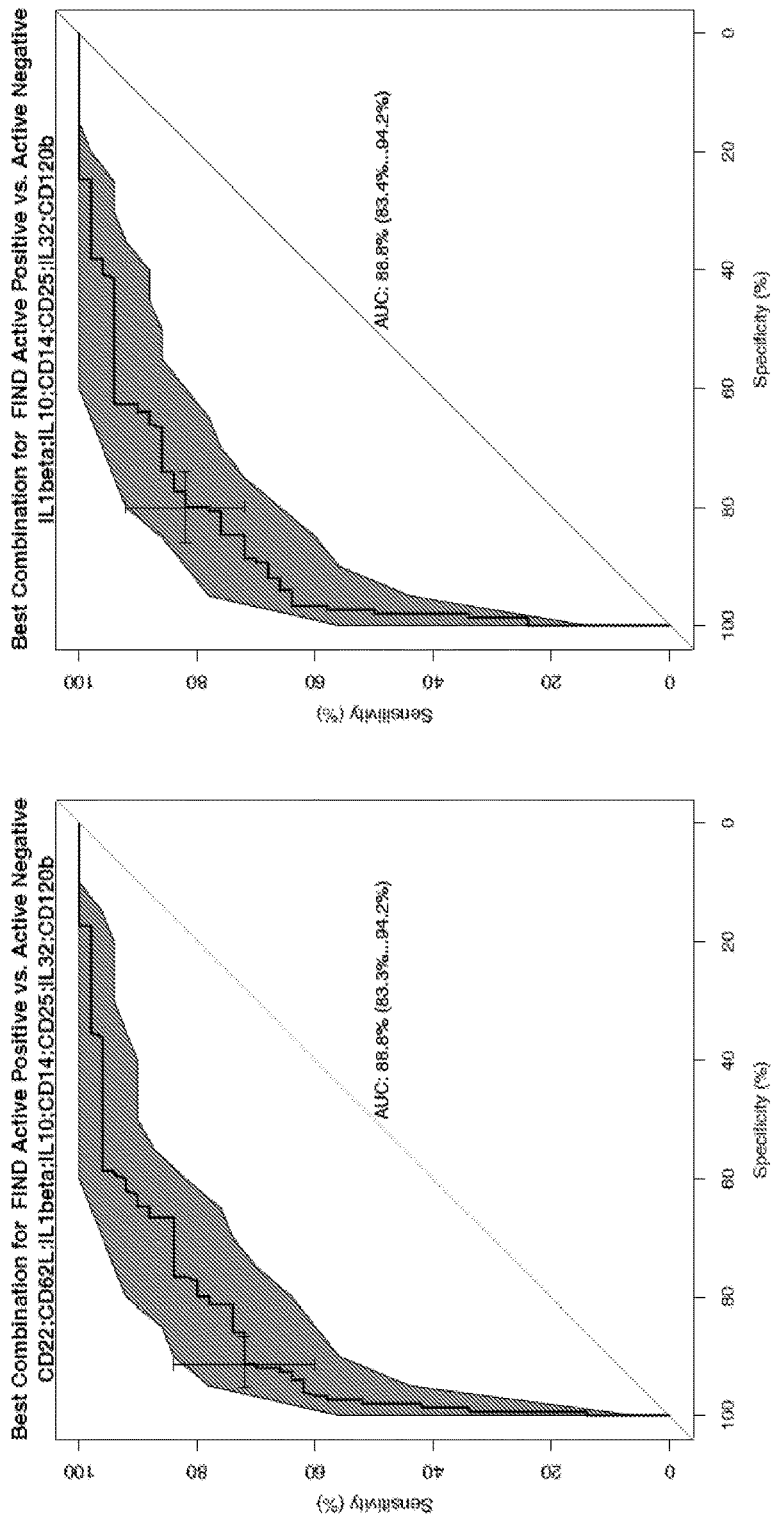
FIG. 24: Two example curves generated from Random Forest classification between samples from Active TB, HIV positive versus Active TB HIV negative to identify the best combinations of biomarkers for differentiation between these groups.

In view of the data presented in FIG. 24, it will be appreciated that references herein to diagnosing, monitoring or treating *tuberculosis* in an individual include references to said individual being co-infected with HIV.

Although it will be appreciated that one or more biomarkers selected from CXCL10, CD64, CD62L and CD54 represent one aspect of the invention, additional biomarkers for diagnosing *tuberculosis* could also be used in order to improve the statistical significance of the diagnosis of *tuberculosis* or of the discriminations between active *tuberculosis* and latent *tuberculosis*; active (smear positive) *tuberculosis* and latent *tuberculosis*; active (smear negative) *tuberculosis* and latent *tuberculosis*; active *tuberculosis* and healthy control(s); latent *tuberculosis* and healthy control(s); active *tuberculosis* and sick control(s); active (smear negative) *tuberculosis* and sick control(s); active (smear positive) *tuberculosis* and sick control(s); latent *tuberculosis* and sick control(s) and active *tuberculosis*, HIV positive and active *tuberculosis*, HIV negative.

Thus, in one embodiment, the use of any of the aforementioned aspects of the invention additionally comprises one or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises two or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises three or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises four or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises five or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises six or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises seven or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises eight or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises nine or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises ten or more further biomarkers selected from: IFN-gamma, IL-10, IL-12p70, IL-1β, IL-6, IL-8, TNF alpha, CD25, CD120b, CD170 and CXCL9.

In a further embodiment, the use of any of the aforementioned aspects of the invention additionally comprises all 11 of the following biomarkers: IFN-gamma, IL-10, IL-12p70, IL-1β, IL-6, IL-8, TNF alpha, CD25, CD120b, CD170 and CXCL9.

In one embodiment, the use of any of the aforementioned aspects of the invention additionally comprises at least IFN-gamma. Data presented herein in Table 4 demonstrates that IFN-gamma provided the single best AUC result for differentiating between (i) active *tuberculosis* and latent *tuberculosis*, (ii) active *tuberculosis* and healthy individuals and (iii) active (smear negative) *tuberculosis* and latent *tuberculosis*.

In one embodiment, the use of any of the aforementioned aspects of the invention additionally comprises at least TNF alpha. Data presented herein in Table 4 demonstrates that TNF alpha provided the single best AUC result for differentiating between symptomatic non-*tuberculosis* individuals and all *tuberculosis* patients (i.e. active and latent *tuberculosis* patients).

In one embodiment, the use of any of the aforementioned aspects of the invention additionally comprises at least IL-10. Data presented herein in Table 4 demonstrates that IL-10 provided the single best AUC result for differentiating between (i) active *tuberculosis* and latent *tuberculosis* and (ii) symptomatic non-*tuberculosis* individuals and active *tuberculosis* patients.

In one embodiment, the use of any of the aforementioned aspects of the invention additionally comprises at least IL-8. Data presented herein in Table 4 demonstrates that IL-8 provided the single best AUC result for differentiating between (i) active (smear positive) *tuberculosis* and latent *tuberculosis*, (ii) active (smear negative) *tuberculosis* and latent *tuberculosis* and (iii) symptomatic non-*tuberculosis* individuals and latent *tuberculosis* patients.

In one embodiment, the use of any of the aforementioned aspects of the invention additionally comprises at least CD25. Data presented herein in Table 4 demonstrates that CD25 provided the single best AUC result for differentiating between (i) healthy individuals and all *tuberculosis* patients (i.e. active and latent *tuberculosis* patients), (ii) active (smear positive) *tuberculosis* and latent *tuberculosis* and (iii) active (smear negative) *tuberculosis* and latent *tuberculosis*.

In one embodiment, the use of any of the aforementioned aspects of the invention additionally comprises at least IL-6. Data presented herein in Table 4 demonstrates that IL-6 provided the single best AUC result for differentiating between active (smear positive) *tuberculosis* and latent *tuberculosis*.

Thus, according to a further aspect of the invention, there is provided the use of each of: CXCL10, CD64, CD62L, CD54, IFN-gamma, IL-10, IL-12p70, IL-1β, IL-6, IL-8, TNF alpha, CD25, CD120b, CD170 and CXCL9 as a specific panel of biomarkers for diagnosing and/or monitoring *tuberculosis*. Data is presented herein in FIGS. 4-16 which demonstrates the effectiveness of the combined panel of 15 markers to differentiate active and latent forms of TB, in particular from differing ethnic backgrounds (i.e. Vietnam and South Africa).

The biomarkers of the invention have the potential to provide a number of key advantages over the existing diagnostic tests for *tuberculosis*. These include rapid diagnosis from serological samples which are relatively easily obtained with no requirement for overnight incubation with RD1 antigens. This is of particular significance in cases of extra pulmonary TB and in paediatric cases where sputum is often swallowed. It also enhances the potential for TB diagnosis in the absence of Category 3 laboratory provisions. The data also supports enhanced diagnostic capability in immunocompromised individuals. Current immunologically based diagnostic adjuncts including the IGRAs, have a low sensitivity and specificity in diagnosing *tuberculosis* in HIV infected individuals, primarily because HIV-infected TB patients produce quantitatively less gamma interferon in response to TB-specific antigens than HIV-negative TB patients (Tsiouris et al (2006) J ClinMicrobiol. 44(8): 2844-2850). By contrast, the biomarkers of the invention may have great utility in the diagnosis of *tuberculosis* (including extrapulmonary *tuberculosis*) in immunocompromised individuals by virtue of the high levels of specificity and sensitivity demonstrated by data shown herein. The data also supports more sensitive and specific discriminations between key clinical discriminations namely: active *tuberculosis* and latent *tuberculosis*; active *tuberculosis* and healthy control(s); latent *tuberculosis* and healthy control(s); active *tuberculosis* and sick control(s); and latent *tuberculosis* and sick control(s).

The biomarkers of the invention also provide the potential for greater comprehension of the immunological response to the disease, and therefore the development of targeted immunotherapy both in respect to the development of immunotherapy for active disease, and the development of post-exposure prophylaxis.

References herein to "*tuberculosis*" include an infectious disease caused by the presence of the pathogen *Mycobacterium tuberculosis*. References to *tuberculosis* also include references to active symptomatic *tuberculosis* infection and latent asympto matic *tuberculosis* infection (LTBI). Most instances of *tuberculosis* infection are primarily restricted to the lungs (i.e. pulmonary *tuberculosis*), however, approximately one quarter of active *tuberculosis* infections move from the lungs, causing other kinds of *tuberculosis*, collectively referred to as extra pulmonary *tuberculosis*. This occurs more commonly in immunosuppressed persons (i.e. those suffering from HIV or AIDS) and young children.

In the context of the invention, the term 'CD' refers to a cell surface leukocyte molecule recognised by a given monoclonal or group of monoclonal antibodies or polyclonal antibodies which specifically 'cluster' to the antigen/molecule in question or a polyclonal antibody. Many, if not all of these CD molecules produce soluble forms that are released from the cell surface by alternative splicing, proteolytic cleavage, dissociation or other mechanisms. Thus in the context of the invention, the termsCD (i.e. soluble CD molecule) is synonymous with the term secreted or soluble or shed CD (sCD). It will be appreciated that references herein to CDs extend also to include sCDs. The term sCD refers to a released form of a leukocyte molecule that is typically found expressed at the cell surface and in which at least a portion of that molecule is recognised by a given monoclonal or group of monoclonal antibodies or polyclonal antibody as herein described. It should be noted however, that the antibody used to recognise the CD molecule may not be a naturally occurring monoclonal or polyclonal antibody. It may be engineered, an artificial construct consisting of an expressed fragment derived from an antibody molecule with intact recognition, or it may be a non-protein molecular recognition agent, or a protein recognition agent, which is not an antibody, or is an antibody hybrid, for example made by introducing antibody binding sites into a different scaffolding.

Advantageously, as defined in WO 03/075016, a soluble form of sCD is generated by various mechanisms including, but not limited to, any of those selected from the group consisting of the following: alternative splicing, proteolytic cleavage and dissociation.

The term "biomarker" refers to a distinctive biological or biologically derived indicator of a process, event, or condition. Biomarkers can be used in methods of diagnosis, e.g.

clinical screening, and prognosis assessment, prediction of active *tuberculosis* disease development (for example from latent infection) and in monitoring the results of therapy, identifying patients most likely to respond to a particular therapeutic treatment, drug screening and development. Biomarkers and uses thereof are valuable for identification of new drug treatments and for discovery of new targets for drug treatment. In particular, the biomarkers of the invention have the potential to effectively monitor the immunological response to anti-TB therapy. For example, it could be easily established which patients have the potential for a shortened course of treatment (currently *tuberculosis* treatment for sensitive strains ranges from 6 to 12 months). They may also form a useful predictive signature which predicts those who will progress to active disease, thereby allowing targeted treatment of a subgroup of latently infected individuals who have a high chance of progressing to active disease.

In view of the fact that the invention is primarily directed to the diagnosis of an infectious disease, drug resistant mutations of *tuberculosis* are of particular concern. For example, certain strains of *tuberculosis* exist which are resistant to particular forms of anti-*tuberculosis* treatment, such as rifampicin resistant *tuberculosis*. The above mentioned "monitoring" aspects of the invention are therefore of critical importance because non-response to treatment can be an early sign that the *tuberculosis* may be rifampicin or multi-drug resistant *tuberculosis*. In this situation, alternative treatment regimes may be employed at a much earlier phase which will allow a greater possibility for the treated individual to survive and decrease transmission.

According to a further aspect of the invention, there is provided a method of diagnosing *tuberculosis* in an individual thereto comprising
a) obtaining a test biological sample from an individual;
b) quantifying the amount of the biomarkers defined herein in the test biological sample; and
c) comparing the amounts of the biomarkers defined herein, in the test biological sample with the amounts present in one or more control samples, wherein a higher level of said biomarker in the test biological sample compared with the control sample is indicative of a diagnosis of *tuberculosis*.

In one embodiment, the higher level is a >1 fold difference relative to the control sample, such as a fold difference of 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15, 20, 25, 30, 35, 40, 45, 50, 55, 60, 65, 70, 75, 80, 85, 90, 95, 100 or any ranges therebetween. In one embodiment, the higher level is between 1 and 75 fold difference relative to the control sample, such as between 1.5 and 10, in particular between 1.5 and 5.

In one embodiment, one or more of the biomarkers may be replaced by a molecule, or a measurable fragment of the molecule, found upstream or downstream of the biomarker in a biological pathway.

In one embodiment, a predictive algorithm base artificial intelligence method is used to compare the amounts of said one or more biomarkers. It will be appreciated by the skilled person that such a predictive algorithm base artificial intelligence method may be conducted in accordance with the cross validation analysis to assess predictive performance as described herein in the Examples section.

As used herein, the term "biosensor" means anything capable of detecting the presence of the biomarker. Examples of biosensors are described herein.

Biosensors according to the invention may comprise a ligand or ligands, as described herein, capable of specific binding to the biomarker. Such biosensors are useful in detecting and/or quantifying a biomarker of the invention.

Diagnostic kits for the diagnosis and monitoring of *tuberculosis* are described herein. In one embodiment, the kits additionally contain a biosensor capable of detecting and/or quantifying a biomarker.

Monitoring methods of the invention can be used to monitor onset, progression, stabilisation, amelioration, remission and/or response to therapeutic intervention. It will also be appreciated that monitoring may also include monitoring the extent of *tuberculosis* to detect the severity of the disease. The markers of the invention may provide differentiation between latent *tuberculosis* and active *tuberculosis*. For example, the invention finds great utility in assisting diagnostic capability both in terms of latent disease, active disease and establishing those with latent disease that may progress to active disease.

In methods of diagnosing and/or monitoring according to the invention, detecting and/or quantifying the biomarker in a biological sample from a test subject may be performed on two or more occasions. Comparisons may be made between the level of biomarker in samples taken on two or more occasions. Assessment of any change in the level of the biomarker in samples taken on two or more occasions may be performed. Modulation of the biomarker level is useful as an indicator of the state of *tuberculosis*. A decrease in the level of the biomarker, over time may be indicative of onset or progression, i.e. worsening of the disorder, whereas an increase in the level of the biomarker indicates amelioration or remission of the disorder, or vice versa.

A method of diagnosis or monitoring according to the invention may comprise quantifying the biomarker in a test biological sample from a test subject and comparing the level of the biomarkes present in said test sample with one or more controls.

The control used in any one of the methods of the invention defined herein may comprise one or more control samples selected from: the level of biomarker found in a healthy control sample from a healthy individual, a healthy biomarker level; or a healthy biomarker range; patients with other respiratory infections; patients with non-TB mycobacterial infections; and patients known to have active or latent TB.

In one embodiment, there is provided a method of diagnosing *tuberculosis*, which comprises:
(a) quantifying the amount of the biomarkers defined herein in a test biological sample; and
(b) comparing the amount of said biomarkers in said test sample with the amount present in one or more control samples.

For biomarkers which are increased in patients with *tuberculosis*, a higher level of the biomarker in the test sample relative to the level in the healthy control is indicative of a diagnosis of *tuberculosis*; an equivalent or lower level of the biomarker in the test sample relative to the healthys control is indicative of absence of *tuberculosis*. For biomarkers which are decreased in patients with *tuberculosis*, a lower level of the biomarker in the test sample relative to the level in the healthy control is indicative of the diagnosis of *tuberculosis*; an equivalent or lower level of the biomarker in the test sample relative to the healthy control is indicative of absence of *tuberculosis*. It will also be appreciated that wherein the control sample comprises a sample obtained from a patient with active or latent *tuberculosis*, a positive diagnosis of active or latent *tuberculosis* will typically require a substantially similar level of the biomarker with the control sample.

The term "diagnosis" as used herein encompasses identification, confirmation, and/or characterisation of *tuberculosis*. Methods of monitoring and of diagnosis according to the invention are useful to confirm the existence of *tuberculosis*; to monitor development of the disorder by assessing onset and progression, or to assess amelioration or regression of the disorder. Methods of monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects).

Also provided is a method of monitoring efficacy of a therapy for *tuberculosis* in a subject having such a disorder, suspected of having such a disorder, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the level of the biomarker(s) in test samples taken on different occasions.

The invention provides a method for monitoring efficacy of therapy for *tuberculosis* in a subject, comprising:
(a) quantifying the amount of the biomarkers defined herein; and
(b) comparing the amount of said biomarkers defined herein, in a test sample with the amount present in one or more control(s) and/or one or more previous test sample(s) taken at an earlier time from the same test subject, such that a difference in the level of the biomarkers in the test sample is indicative of a response to the treatment.

For biomarkers which are increased in patients with *tuberculosis*, a decrease in the level of the biomarker in the test sample relative to the level in a previous test sample taken earlier from the same test subject is indicative of a beneficial effect, e.g. stabilisation or improvement, of said therapy on the disorder. For biomarkers which are decreased in patients with *tuberculosis*, an increase in the level of the biomarker in the test sample relative to the level in a previous test sample taken earlier from the same test subject is indicative of a beneficial effect, e.g. stabilisation or improvement, of said therapy on the disorder.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 months, 12 months, 18 months or 24 months. Samples may be taken prior to and/or during and/or following treatment. Samples can be taken at intervals over the remaining life, or a part thereof, of a subject.

The term "detecting" as used herein means confirming the presence of the biomarker present in the sample. Quantifying the amount of the biomarker present in a sample may include determining the concentration of the biomarker present in the sample. Detecting and/or quantifying may be performed directly on the sample, or indirectly on an extract therefrom, or on a dilution thereof.

In alternative aspects of the invention, the presence of the biomarker is assessed by detecting and/or quantifying antibody or fragments thereof capable of specific binding to the biomarker that are generated by the subject's body in response to the biomarker and thus are present in a biological sample from a subject having *tuberculosis*.

Detecting and/or quantifying can be performed by any method suitable to identify the presence and/or amount of a specific biomarker in a biological sample from a patient or a purification or extract of a biological sample or a dilution thereof. In methods of the invention, quantifying may be performed by measuring the concentration of the biomarker in the sample or samples. Biological samples that may be tested in a method of the invention include whole blood, serum, plasma, tissue fluid, cerebrospinal fluid (CSF), synovial fluid, follicular fluid, seminal fluid, amniotic fluid, milk, urine, pleural fluid, ascites, bronchoalveolar lavage, saliva, sputum, tears, perspiration, lymphatic fluid, aspirate, bone marrow aspirate and mucus, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner. In one embodiment, the biological sample comprises whole blood, serum or plasma. In a further embodiment, the biological sample comprises serum, such as non-activated or unstimulated serum.

Detection and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI(-TOF), a 1-D gel-based analysis, a 2-D gel-based analysis, Mass spectrometry (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing and/or monitoring according to the invention may comprise analysing a plasma, serum or whole blood sample by a sandwich immunoassay to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the biomarkers may be performed using an immunological method, involving an antibody, or a fragment thereof capable of specific binding to the biomarker. Suitable immunological methods include sandwich immunoassays, such as sandwich ELISA, in which the detection of the biomarkers is performed using two antibodies which recognize different epitopes on a biomarker; radio immunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

Immunological methods in accordance with the invention may be based, for example, on any of the following methods.

Immunoprecipitation is the simplest immunoassay method; this measures the quantity of precipitate, which forms after the reagent antibody has incubated with the sample and reacted with the target antigen present therein to form an insoluble aggregate. Immunoprecipitation reactions may be qualitative or quantitative.

In particle immunoassays, several antibodies are linked to the particle, and the particle is able to bind many antigen molecules simultaneously. This greatly accelerates the speed of the visible reaction. This allows rapid and sensitive detection of the biomarker.

In immunonephelometry, the interaction of an antibody and target antigen on the biomarker results in the formation of immune complexes, which are too small to precipitate. However, these complexes will scatter incident light and this can be measured using a nephelometer. The antigen, i.e. biomarker, concentration can be determined within minutes of the reaction.

Radioimmunoassay (RIA) methods employ radioactive isotopes such as $I^{125}$ to label either the antigen or antibody. The isotope used emits gamma rays, which are usually measured following removal of unbound (free) radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme immunoassays.

Enzyme (EIA) immunoassays were developed as an alternative to radio immunoassays (RIA). These methods use an enzyme to label either the antibody or target antigen. The sensitivity of EIA approaches that for RIA, without the danger posed by radioactive isotopes. One of the most widely used EIA methods for detection is the enzyme-linked immunosorbent assay (ELISA). ELISA methods may use two antibodies one of which is specific for the target antigen and the other of which is coupled to an enzyme, addition of the substrate for the enzyme results in production of a chemiluminescent or fluorescent signal.

Fluorescent immunoassay (FIA) refers to immunoassays which utilize a fluorescent label or an enzyme label which acts on the substrate to form a fluorescent product. Fluorescent measurements are inherently more sensitive than colorimetric (spectrophotometric) measurements. Therefore, FIA methods have greater analytical sensitivity than EIA methods, which employ absorbance (optical density) measurement.

Chemiluminescent immunoassays utilize a chemiluminescent label, which produces light when excited by chemical energy; the emissions are measured using a light detector.

Immunological methods according to the invention can thus be performed using well-known methods. Any direct (e.g., using a sensor chip) or indirect procedure may be used in the detection of biomarkers of the invention.

The Biotin-Avidin or Biotin-Streptavidin systems are generic labelling systems that can be adapted for use in immunological methods of the invention. One binding partner (hapten, antigen, ligand, aptamer, antibody, enzyme etc) is labelled with biotin and the other partner (surface, e.g. well, bead, sensor etc) is labelled with avidin or streptavidin. This is conventional technology for immunoassays, gene probe assays and (bio)sensors, but is an indirect immobilisation route rather than a direct one. For example a biotinylated ligand (e.g. antibody or aptamer) specific for a biomarker of the invention may be immobilised on an avid in or streptavidin surface, the immobilised ligand may then be exposed to a sample containing or suspected of containing the biomarker in order to detect and/or quantify a biomarker of the invention. Detection and/or quantification of the immobilised antigen may then be performed by an immunological method as described herein.

The term "antibody" as used herein includes, but is not limited to: polyclonal, monoclonal, bispecific, humanised or chimeric antibodies, single chain antibodies, fragments (such as FAb, F(Ab')$_2$, Fv, disulphide linked Fv, scFv, diabody), fragments produced by a Fab expression library, anti-idiotypic (anti-Id) antibodies and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, detecting and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

Thus, according to a further aspect of the invention there is provided an apparatus for diagnosing and/or monitoring *tuberculosis* which comprises a biosensor, microanalytical, microengineered, microseparation and/or immunochromatography system configured to detect and/or quantify any of the biomarkers defined herein.

Suitably, biosensors for detection of one or more biomarkers of the invention combine biomolecular recognition with appropriate means to convert detection of the presence, or quantitation, of the biomarker in the sample into a signal.

Biosensors can be adapted for "alternate site" diagnostic testing, e.g. in the ward, outpatients' department, surgery, home, field and workplace.

Biosensors to detect one or more biomarkers of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the one or more biomarkers of the invention.

Levels of the biomarkers of the invention may be measured in accordance with any of the techniques described hereinbefore. In one particular embodiment, the levels of IFN-gamma and TNF-alpha may be measured in accordance with an MSD® assay, such as the Human Pro-inflammatory 7-Plex Assay Ultra-Sensitive Kit (Mesoscale Discovery; Catalogue No. K15008C-1, K15008C-2 or K15008C-4).

This Pro-inflammatory assay detects IFN-gamma or TNF-alpha in a sandwich immunoassay format by providing a plate which has been pre-coated with capture antibody on spatially distinct spots. A sample is then added to the plate along with a solution containing anti-IFN-gamma or anti-TNF-alpha detection antibodies labelled with an electro chemiluminescent compound and incubated for a specified time period. IFN-gamma or TNF-alpha within the sample will bind to capture antibodies immobilised on the working electrode surface and recruitment of the labelled detection antibodies by bound IFN-gamma analytes or TNF-alpha analytes completes the sandwich. An MSD read buffer is then added to provide a chemical environment for electro chemiluminescence and the plate is then loaded into an MSD SECTOR® instrument for analysis. Inside the SECTOR instrument, a voltage applied to the plate electrodes causes the labels bound to the electrode surface to emit light. The instrument measures intensity of emitted light to afford a quantitative measure of IFN-gamma or TNF-alpha present in the sample. It will be appreciated that other cytokines and chemokines (such as IL-10, IL-12 p70, IL-1β, IL-6, IL-8 or IL-32) may be quantified in accordance with analogous procedures described above for IFN-gamma and TNF-alpha.

When the biomarker comprises a CD molecule, such as CD14, CD22, CD25, CD27, CD120b, CD170, CD64, CD62L or CD54, levels may be measured from samples of serum or plasma or other body fluids using reagents suitable for detecting soluble CDs that include but are not limited to antibodies raised against those CDs. In one embodiment, monoclonal antibodies or engineered antibodies, including phage antibodies raised against the sCDor their membrane bound form are used for their detection. However, non-protein agents may also in principle be used to detect sCDs. Similarly the detecting molecule may contain antibody binding site fragments incorporated into the scaffold of another molecule or an engineered scaffold. Commercially available kits for measuring CD levels include those from Diaclone 1, BdA Fleming BP 1985 F-25020 Besancon Cedex-France and Medsystems Diagnostics GmbH, Rennweg 95b, A-1030 Vienna Austria.

Suitable techniques for measuring sCDs include but are not limited to immunoassays including ELISA using commercially available kits such as those described above, flow cytometry particularly multiplexed particle flow cytometry as herein described. Those skilled in the art will be aware of other suitable techniques for measuring CD levels in samples from an individual including antibody 'chip' array type technologies or chip technologies utilizing non-classical antibody binding site grafted molecules.

In one particular embodiment, the method of measuring sCDsor chemokines such as CXCL9 and CXCL10 comprises an MSD® assay as defined hereinbefore with the modifications described herein.

Methods involving detection and/or quantification of one or more biomarkers of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-neuromedicine.

Any suitable animal may be used as a subject non-human animal, for example a non-human primate, horse, cow, pig, goat, sheep, dog, cat, fish, rodent, e.g. guinea pig, rat or mouse; insect (e.g. *Drosophila*), amphibian (e.g. *Xenopus*) or *C. elegans*.

The test substance can be a known chemical or pharmaceutical substance, such as, but not limited to, an anti-depressive disorder therapeutic; or the test substance can be a novel synthetic or natural chemical entity, or a combination of two or more of the aforesaid substances.

There is provided a method of identifying a substance capable of promoting or suppressing the generation of the biomarker in a subject, comprising exposing a test cell to a test substance and monitoring the level of the biomarker within said test cell, or secreted by said test cell.

The test cell could be prokaryotic, however a eukaryotic cell will suitably be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin.

In methods for identifying substances of potential therapeutic use, non-human animals or cells can be used that are capable of expressing the biomarker.

Screening methods also encompass a method of identifying a ligand capable of binding to the biomarker according to the invention, comprising incubating a test substance in the presence of the biomarker in conditions appropriate for binding, and detecting and/or quantifying binding of the biomarker to said test substance.

High-throughput screening technologies based on the biomarker, uses and methods of the invention, e.g. configured in an array format, are suitable to monitor biomarker signatures for the identification of potentially useful therapeutic compounds, e.g. ligands such as natural compounds, synthetic chemical compounds (e.g. from combinatorial libraries), peptides, monoclonal or polyclonal antibodies or fragments thereof, which may be capable of binding the biomarker.

Methods of the invention can be performed in array format, e.g. on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of inhibiting, directly or indirectly, the activity of the biomarker, or of suppressing generation of the biomarker. The term "substances" includes substances that do not directly bind the biomarker and directly modulate a function, but instead indirectly modulate a function of the biomarker. Ligands are also included in the term substances; ligands of the invention (e.g. a natural or synthetic chemical compound, peptide, aptamer, oligonucleotide, antibody or antibody fragment) are capable of binding, suitably specific binding, to the biomarker.

The invention further provides a substance according to the invention for use in the treatment of *tuberculosis*.

Also provided is the use of a substance according to the invention in the treatment of *tuberculosis*.

Also provided is the use of a substance according to the invention as a medicament.

Yet further provided is the use of a substance according to the invention in the manufacture of a medicament for the treatment of *tuberculosis*.

According to a further aspect of the invention, there is provided a method of treating *tuberculosis* in an individual in need thereof, wherein said method comprises the following steps:
 (a) diagnosing *tuberculosis* in an individual according to the method described herein; followed by
 (b) administering an anti-*tuberculosis* medicament to said individual in the event of a positive diagnosis for *tuberculosis*.

According to a further aspect of the invention, there is provided a method of treating *tuberculosis* in an individual in need thereof, which comprises the step of administering an anti-*tuberculosis* medicament to a patient identified as having differing levels of the biomarkers as defined herein when compared to the levels of said biomarkers from a control subject.

In one embodiment, said anti-*tuberculosis* medicament is: one or more first line medicaments selected from: ethambutol, isoniazid, pyrazinamide, rifampicin; and/or one or more second line medicaments selected from: aminoglycosides (e.g., amikacin, kanamycin), polypeptides (e.g., capreomycin, viomycin, enviomycin), fluoroquinolones (e.g., ciprofloxacin, levofloxacin, moxifloxacin), thioamides (e.g. ethionamide, prothionamide), cycloserine (closerin) or terizidone; and/or one or more third line medicaments selected from rifabutin, macrolides (e.g., clarithromycin), linelid, thioacetazone, thioridazine, arginine, vitamin D and R207910.

A kit for diagnosing and/or monitoring *tuberculosis* is provided. Suitably a kit according to the invention may contain one or more components selected from the group: a ligand specific for the biomarker or a structural/shape mimic of the biomarker, one or more controls, one or more reagents and one or more consumables; optionally together with instructions for use of the kit in accordance with any of the methods defined herein. In one embodiment, the kit differentially diagnoses active and latent *tuberculosis*.

The identification of biomarkers for *tuberculosis* permits integration of diagnostic procedures and therapeutic regimes. Currently there are significant delays in determining effective treatment and hitherto it has not been possible to perform rapid assessment of drug response. Traditionally, many *tuberculosis* therapies have required treatment trials lasting weeks to months for a given therapeutic approach. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum or plasma drug levels. The biomarkers may be used to provide warning of adverse drug response. Biomarkers are useful in development of personalized therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, in a time frame and with precision, not achievable using the current subjective measures.

Biomarker monitoring methods, biosensors and kits are also vital as patient monitoring tools, to enable the physician to determine whether relapse is due to worsening of the disorder, poor patient compliance or drug resistance. In particular, the invention may also be used to monitor patient compliance with taking a particular drug (agent), and/or undergoing a particular treatment regime.

If pharmacological treatment is assessed to be inadequate, then therapy can be reinstated or increased; a change in therapy can be given if appropriate. As the biomarkers are sensitive to the state of the disorder, they provide an indication of the impact of drug therapy.

The following studies illustrate the invention.

Example 1: Effectiveness of CXCL10, sCD64, sCD62L and sCD54 as TB Biomarkers

The use of CXCL10, sCD64, sCD62L and sCD54 and additional CDs were assessed for their effectiveness to discriminate between different sample classes (healthy, latent TB, active TB, sick). Retrospective samples were used that were previously frozen and shipped at −80° C. to the UK.

The summary of patients by country of origin and category is provided in Table 1 below:

TABLE 1

Summary of Samples By Country of Origin and Type

| | Healthy | Latent TB | Active TB (smear pos) | Active TB (smear neg) | Symptomatic Non-TB (Sick) |
|---|---|---|---|---|---|
| South Africa | 26 | 68 | 100 | | |
| Vietnamese | | 47 | 92 | 47 | 44 |

Here latent is defined as latent infection and may be determined clinically in combination with IGRA test or Mantoux test. Active refers to active TB test. All of these Active TB as well as having clinical symptoms were culture confirmed (Mtb cells were found in cultured sputum after 2-5 weeks, this is the gold standard).

Some were smear test positive as well, some were smear test negative. Symptomatic Non-TB (listed also herein as "Sick" or "non-TB") were patients who presented with symptoms similar to TB in the clinic but were smear and culture (and later clinically) confirmed not to have TB.

South African Cohort

Serum samples were obtained from two groups classified as latent *tuberculosis* and active pulmonary *tuberculosis*. To be eligible for enrolment individuals had to be between 18-65 yrs and willing to undergo an HIV test. Individuals unable or unwilling to sign a consent form and those that were pregnant were excluded. Only those with negative HIV results were included.

Active disease was defined as individuals with sputum auramine smear positive and Mycobacterial Growth Indicator Tube (MGIT) culture positive results. This cohort were treatment naïve (i.e. all samples were collected before the initiation of TB treatment) and recruited from primary health care clinics in Capetown. The latent *tuberculosis* cohort was derived from adult healthcare workers employed at primary and secondary health care facilities. Latent disease was defined as a positive interferon gamma release assay (IGRA) in the absence of Chest X-ray (CXR) changes or active symptoms of *tuberculosis* as certained by questionnaire.

Vietnamese Cohort

Serum samples were obtained from three groups classified as latent, active pulmonary *tuberculosis* and sick controls. Those with active pulmonary disease were sub-grouped into those with Ziehl-Neelson smear positive and smear negative results.

Those in the latent cohort were collected from Vietnamese visa applicants to the US during the standard immigrant medical examination at the Cho Ray Hospital Medical Visa Unit as part of a study performed by Painter et al 2013. Samples were taken from individuals recruited between December 2008 and January 2010. Individuals over the age of 18 years who were able to provide informed consent were included. Latent disease was defined as individuals with positive IGRA results and a normal CXR. Universal testing for HIV was required of all US immigrant applicants during samples collection. No positive individuals were identified within the latent cohort.

The active cohort was recruited from patients suspected to have *tuberculosis* presenting to Pham Ngoc Thach Hospital (tertiary pulmonary referral centre) in Ho Chi Min city between 2007-2008. The study recruited individuals presenting with symptoms suggesting pulmonary *tuberculosis* defined as cough for >3 weeks in conjunction with one of the following fever, malaise, recent weight loss, night sweats, contact with known case of active pulmonary *tuberculosis*, haemoptysis, chest pain or loss of appetite. Individuals over the age of 18 years and able to provide informed consent for sample collection, banking and HIV testing were included. Patients who had received anti-tuberculous therapy including fluoroquinolones and aminoglycosides in the 60 days prior to enrolment, who had only extra-pulmonary disease and those for whom good follow-up and a clear final diagnosis were deemed difficult (ie transient residents) were excluded. Patients unable to expectorate were also excluded. Patients with a prior history or TB who had not received anti-tuberculous therapy for sixty days and women of child bearing age who might have been pregnant were not excluded. Only samples from HIV negative individuals were included in analysis.

Participants provided a standard of 2 smears and 4 cultures (2× Lowenstein Jensen (LJ), 2×MGIT, species confirmation done for positive cultures). Individuals who on initial assessment had at least 1 positive smear ≥1 positive or ≥2 positive scanty smears and at least 1 TB positive culture were defined as smear positive and culture positive. Those on initial assessment with ≥2 negative smears or 1 scanty smear and ≥1 negative smear and ≥1 TB positive culture were defined as smear negative, culture positive. The sick control group were defined as those who were both smear and TB sputum culture negative at initial presentation in addition to fulfilling further criteria at eight week follow-up. These included significant clinical improvement and a CXR, if initially abnormal, which was not suggestive of TB, normal or stably abnormal.

Further details concerning diagnosis of Vietnam patients is shown in Table 2:

TABLE 2

Example diagnostic protocols (in this case for determining active TB in Vietnam active TB samples).

| Category | Diagnosis | Smear | Culture | Description | Initial CXR | Microbiological follow-up (FU) (2 months) | Clinical and radiographic findings during FU |
|---|---|---|---|---|---|---|---|
| SS+ | TB, smear positive | pos | pos | On initial assessment at least 1 pos smear ≥1+ or ≥2 scanty pos smears and at least 1 MTB pos culture (see definition) | Not applicable (NA) | NA | NA |
| C+ | TB, smear negative, culture positive | neg | pos | On initial assessment ≥2 neg smears or 1 scanty smear and ≥1 neg smear and ≥1 MTB pos culture (see definition) | abnormal (except HIV pos) | NA | NA |

TABLE 2-continued

Example diagnostic protocols (in this case for determining active TB in Vietnam active TB samples).

| CXR+ | TB, culture negative (treated) | neg | neg | ≥2 neg smears and only MTB neg cultures, pos CXR, and response to TB tx | abnormal AND → | NA | Clinical and radiographic improvement under TB tx |
|---|---|---|---|---|---|---|---|
| Non-TB | Non-TB (untreated) | neg | neg | ≥2 neg smears and cultures on initial and FU assessment | NA | Smear and culture negative | Significant clinical improvement and CXR -if initially abnormal- not TB suggestive, normal or stable abnormal |
| F | TB, diagnosed during FU | in FU neg or pos | in FU pos | Initially neg smears and cultures, but MTB pos culture during FU | irrelevant | Pos in culture or smear and culture | Clinical symptoms of TB |
| I | Indeterminate | Any other combination of results not matching other categories. | | | | | |

Laboratory Methodology

In the South Africa cohort, blood was collected at clinic locations using additive-free vacutainer tubes. It was transported to the laboratory within 4 hours and then centrifuged. Aliqouts were frozen at −80° and shipped on dry ice to the UK laboratory. Both sample collections were shipped in accordance with International shipping protocols.

In the Vietnamese cohort, blood was collected using additive-free vacutainer tubes (red cap), allowed to clot for up to 60 min at room temperature, centrifuged for 10 minutes at ≤1300 RCF (RT) and aliquoted in 0.5 ml into 1.0 or 2.0 ml cryovials. Aliquots were frozen on site at −70° C. and shipped on dry ice via the FIND repository.

The analyses were conducted by detecting the amounts of a large number of potential biomarkers using a Meso Scale Discovery® (MSD) assay. For example, the biomarkers of the invention were detected as follows:

IFN Gamma, IL-10, IL-12 p70, IL-1β, IL-6, IL-8, IL-32 and TNF Alpha

These markers were quantified using a Human Pro-inflammatory 7-Plex Assay (Meso Scale Discovery Catalogue Numbers K15008C-1, K15008C-2 or K15008C-4) exactly in accordance with the manufacturer's instructions. It will be appreciated that other cytokines and chemokines may be quantified in accordance with analogous procedures described above for IFN-gamma and TNF-alpha.

CXCL10, CD14, CD22, CD25, CD27, CD120b, CD170, CD64, CD62L, CD54, CXCL9

These markers were quantified using a modified Meso Scale Discovery assay by using the following reagents and protocol:

Reagents Used
Human IGF-IIR (DuoSet DY2447 from R&D systems: Lot 1272152: expiry 25.10.15)
Capture Antibody
Diluted 1 in 180 in PBS (19 μl in 3.5 ml)
Pipetted 30 μl/well of an MSD standard bind plate
Seal+Incubate at +4 overnight
Wash ×3 with MSD wash buffer
Block for a minimum of 1 hour with 150 μl MSD Blocker A
Wash ×1 with MSD wash buffer
Standard
Reconstitute with 0.5 ml 1% BSA/PBS=290 ng/ml=290,000 pg/ml
Dilute 1 in 5 in DELFIA Dil II=58,000 pg/ml (50+200)= std 7
Then serially dilute 1 in 2 in DELFIA Dil II (100+100)= 29000, 14500, 7250, 3625, 1813, +0 pg/ml
QCs: 1=pooled plasma 1.2.11
2=spiked plasma 1.2.11
3=spiked pool 26.7.10
Assay
Pipette 40 μl DELFIA Dil II/well+10 μl std/QC/unknown in duplicate
Cover & incubate on a plate shaker 2 hours at Room Temperature
Wash ×3 with MSD wash buffer
Biotinylated Antibody
Dilute the antibody 1 in 180 in MSD Diluent 100 (19 μl in 3.5 ml)
Add 25 μl/well
Cover and incubate on a plate shaker 1 hour at RT
Wash ×3 with MSD wash buffer
Strepavidin-SulphoTAG
Dilute 1 in 1000 in MSD Diluent 100 (3 μl in 3 ml)
Add 25 μl/well
Cover and incubate on a plate shaker for 30 minutes at Room Temperature
Wash ×3
150 μl read buffer+read on MSD Sector 6000® reader
Results are calculated using MSD Workbench Software® package It will be appreciated that other chemokine and soluble cluster of differentiation (sCD) molecules may be quantified in accordance with analogous procedures described above.

Statistical Methodology

The dataset was prepared for analysis in the following manner using the R statistical environment (R Development Core Team, 2008): a $\log_2$ transformation was applied to the data set before a t-test was applied for each comparison group. The antigens were ranked by adjusted p-values for multiple testing correction using the Benjamani & Hochberg (1995) approach. Hierarchical clustering and principal components analysis was performed using the packages hclust and pca Methods respectively, and the package heatmap.plus was used to create heatmaps of the data.

For the Random Forest classification (Brieman& Forest, 2001) of the data into the main clinical groupings, a random sampling of the data-set was used for the construction of the decision tree: half was used as a training set while the other half was used as a validation set and vice versa. To investigate which is the best combination of markers for discriminating between the clinical TB groups, the mean decrease in accuracy measure (Diaz-Uriarte, R. and Alvarez de Andres, 2006) was used to rank the importance of each marker in the prediction. This involved calculating Area Under the Curve (AUC) scores for varying combinations of antigens using a 'leave-one-out' approach, starting with removal of the least important marker and then eliminating it when there is an improvement or no change in the overall AUC score. Data from an independent cohort was used to validate the final 'best combination' of markers with the highest AUC score.

The R package random Forest was used for the Random Forest classification and in computing the measures of variable importance. The AUC scores were calculated using the ROCR and pROC packages (Sing et al. 2005; Robin et al. 2007) and AUC plots were produced using the latter package.

Results

Raw Data Processing and Normalization

Antigen levels were variance stabilized to decouple the relationship between mean expression level and technical replicate variance. This transformation approximately corresponds to log transforming the data with an additional offset and scale and is standard for most microarray analysis. The results are shown in Table 3 below:

TABLE 3

Differentiation Expression Analysis (FDR adjusted p-values)

| Gene | Active-Latent | Latent-Healthy | Active-Sick |
|---|---|---|---|
| IFN-gamma | 2.25E−49 | 1.00E+00 | 7.33E−09 |
| IL-10 | 2.68E−14 | 2.89E−02 | 1.00E+00 |
| IL-12p70 | 1.00E+00 | 1.00E+00 | 1.00E+00 |
| IL-1β | 2.01E−01 | 9.51E−01 | 1.90E−01 |
| IL-6 | 6.21E−37 | 1.90E−01 | 2.02E−06 |
| IL-8 | 1.00E+00 | 3.71E−01 | 1.00E+00 |
| TNF alpha | 1.18E−20 | 2.14E−03 | 7.93E−01 |

TABLE 3-continued

Differentiation Expression Analysis (FDR adjusted p-values)

| Gene | Active-Latent | Latent-Healthy | Active-Sick |
|---|---|---|---|
| CXCL10 (IP-10) | 2.38E−43 | 9.51E−01 | 1.88E−02 |
| CD25 (IL2RA) | 6.32E−58 | 1.00E+00 | 1.10E−11 |
| CD120b (TNFRSF1B) | 4.28E−25 | 1.00E+00 | 5.36E−05 |
| CD170 (SIGLEC5) | 1.00E+00 | 1.00E+00 | 6.81E−01 |
| CD64 (FCGR1A) | 1.87E−24 | 1.00E+00 | 1.22E−12 |
| CD62L (SELL) | 6.67E−09 | 1.00E+00 | 8.00E−02 |
| CD54 (ICAM) | 3.09E−29 | 1.00E+00 | 7.01E−08 |
| CXCL9 | 1.45E−46 | 9.51E−01 | 4.32E−07 |

Cross Validation Analyses to Assess Predictive Performance

We assessed the predictive ability of alternative combinations of antigens for the task of discriminating different sample classes. All experiments were conducted using 10-fold cross validation. For each fold, the fraction of 9/10 of the data were used to train a non-linear support vector machine (SVM) classifier to predict the sample label of the remaining 1/10 of the samples. The prediction accuracy was assessed and reported using the area under the receiver operating characteristics (AUC). A perfect predictor would yield an AUC of 1.0, whereas a random predictor corresponds to an AUC of 0.5 when the sample set is balanced. A consistently failing predictor would yield an AUC of 0.0. To assess the reliability of the results obtained, all experiments were repeated in triplicates for alternative random seeds used for each experiment. We report mean performance across these prediction experiments and variability as plus and minus one standard deviation estimates.

Table 4 shows the predictive performance for these alternatives and for different prediction tasks. The combination of the complete panel of 15 biomarkers (i.e. IFN gamma, IL-10, IL-12 p70, IL-1β, IL-6, IL-8, TNF alpha, CXCL10, CD25, CD120b, CD170, CD64, CD62L, CD54 and CXCL-9 consistently outperforms the single-antigen based approach.

TABLE 4

Predictive performance of antigens for alternative classification tasks

| Prediction | Specifics | Country | AUC For 15 marker panel | AUC best single antigen |
|---|---|---|---|---|
| Active/Latent | | SA | 1.00 | 1.00 (IFN-gamma) |
| Active/Healthy | | SA | 1.00 | 1.00 (IFN-gamma) |
| Active/Sick | Smear negative | VN | 0.73 | 0.65 (CD62L) |
| Active/Active | Smear negative/ Smear positive | VN | 0.73 | 0.73 (IP10) |
| Active/Sick | Smear positive | VN | 0.90 | 0.85 (CD64) |
| Sick/TB | | VN | 0.71 | 0.73 (TNFalpha) |
| Active/Latent | | VN | 0.90 | 0.91 (IL-10) |
| Active/Latent | Smear positive | VN | 0.95 | 0.94 (IL-8) |
| Active/Latent | Smear negative | VN | 0.8 | 0.79 (IL-8) |
| Healthy/TB | | SA | 0.67 | 0.66 (CD25) |
| Sick/Active | | VN | 0.83 | 0.71 (IL-10) |
| Sick/Latent | | VN | 0.59 | 0.58 (IL-8) |
| Active/Latent | Smear negative | SA->VN | 0.66 | 0.77 (IFN-gamma) |
| Active/Latent | Smear positive | SA->VN | 0.90 | 0.90 (CD25) |
| Active/Latent | Smear negative | VN->SA | 0.84 | 0.86 (CD25) |
| Active/Latent | Smear positive | VN->SA | 0.89 | 0.86 (IL6) |

Key: SA=South Africa, VN=Vietnam, Smear negative=Smear test negative. So for example Active/latent, smear negative, SA→VN means that the training set was Active TB and latent TB samples from South Africa only (all South African active TB samples were from smear positive patients) and the resultant predictive test was then applied to smear negative Vietnamese samples. The AUC was 0.66 for this analysis. All Active TB samples are confirmed culture positive. Sick/TB means Symptomatic Non-TB vs all TB (active and latent TB)

As can be seen the combinations of individual biomarkers sometimes added additional accuracy further than that seen with a single best biomarker.

Example 2: Analysis of Further Combination of TB Biomarkers

This study was conducted in an analogous manner to that described in Example 1 hereinbefore using samples from the cohorts described in Table 5.

TABLE 5

Summary of Samples By Country of Origin and Type

|  | Peru | South Africa | Vietnam |
|---|---|---|---|
| Latent TB |  |  | 16 |
| Symptomatic Non-TB (Sick) | 14 | 40 | 30 |
| Active TB (Smear Neg) | 7 | 21 | 82 |
| Active TB (Smear Pos) | 20 | 20 | 50 |
| Active TB, HIV Negative | 27 | 15 | 108 |
| Active TB, HIV Positive |  | 26 | 24 |
| Latent, HIV Negative |  |  | 16 |
| Non-TB, HIV Negative | 14 | 20 | 30 |
| Non-TB, HIV Positive |  |  | 20 |

Statistical analyses were conducted in an analogous manner to that described in Example 1 between the following 8 groups:
Active TB versus Latent TB;
Active TB versus Symptomatic Non-TB (Sick);
Latent TB versus Symptomatic Non-TB (Sick);
Active TB (Smear Neg) versus Latent TB;
Active TB (Smear Neg) versus Symptomatic Non-TB (Sick);
Active TB (Smear Pos) versus Latent TB;
Active TB (Smear Pos) versus Symptomatic Non-TB (Sick); and
Active TB, HIV positive versus Active TB HIV negative.

Each analysis was run twice and the results of all analyses can be seen in FIGS. 17 to 24 wherein certain specific markers according to the invention have been identified as providing the best combinations (AUC ranging from 80.8% to 99.9%).

The invention claimed is:

1. A method of treating active (smear positive) *tuberculosis* in an individual, wherein the method comprises:
   (a) differentially diagnosing active (smear positive) *tuberculosis* over latent *tuberculosis* in the individual, comprising:
      (1) obtaining a test biological sample from an individual;
      (2) quantifying the amount of three or more biomarkers selected from CD14, CD22, CD25, CD64, IL-10, CXCL10, and IFN gamma, wherein at least one of the biomarkers is IFN gamma and at least one of the biomarkers is IL-10; and
      (3) comparing the amounts of the biomarkers in the test biological sample with the amounts present in one or more control samples, such that a difference in the level of the biomarkers in the test biological sample is indicative of a differential diagnosis of active (smear positive) *tuberculosis* over latent *tuberculosis*; followed by
   (b) administering an anti-*tuberculosis* medicament to the individual if there is a positive diagnosis for active (smear positive) *tuberculosis*.

2. The method of claim 1, wherein the *tuberculosis* is active (smear positive) *tuberculosis* and is extrapulmonary *tuberculosis*.

3. The method of claim 1, wherein the anti-*tuberculosis* medicament comprises one or more of
   (a) one or more first line medicaments selected from ethambutol, isoniazid, pyrazinamide, and rifampicin;
   (b) one or more second line medicaments selected from aminoglycosides, amikacin, kanamycin, polypeptides used to treat *tuberculosis*, capreomycin, viomycin, enviomycin, fluoroquinolones, ciprofloxacin, levofloxacin, moxifloxacin, thioamides, ethionamide, prothionamide, cycloserine, closerin, and terizidone; and
   (c) one or more third line medicaments selected from rifabutin, macrolides, clarithromycin, linezolid, thioacetazone, thioridazine, arginine, vitamin D, and R207910.

4. The method of claim 1, wherein the comparing comprises using a predictive algorithm method to compare the amounts of one or more of the biomarkers.

5. The method of claim 1, wherein samples are taken on two or more occasions from the individual.

6. The method of claim 1, further comprising comparing the level of the biomarkers in samples taken on two or more occasions.

7. The method of claim 1, comprising comparing the amount of the biomarkers in the test sample with the amount present in (a) one or more samples taken from the individual prior to commencement of therapy, (b) one or more samples taken from the individual at an earlier stage of therapy; or (c) both.

8. The method of claim 1, further comprising detecting a change in the amount of the biomarkers in samples taken on two or more occasions.

9. The method of claim 1, wherein the amount of the biomarkers in the test sample is compared with more than one control sample.

10. The method of claim 1, wherein the one or more control samples comprise control samples selected from a level of analyte biomarker found in a healthy control sample from a healthy individual; a healthy analyte biomarker level; a healthy analyte biomarker range; patients with other respiratory infections; patients with non-TB mycobacterial infections;
and patients known to have active or latent TB.

11. The method of claim 10, wherein the amount of the biomarkers in the test sample is compared with more than one control sample.

12. The method of claim 1, wherein samples are obtained from one or more of (a) prior to therapy for *tuberculosis*, (b) during therapy for *tuberculosis*, and (c) following therapy for *tuberculosis*.

13. The method of claim 1, wherein samples are taken at intervals over the remaining life, or a part thereof, of the individual.

14. The method of claim 1, wherein the quantifying is performed by measuring the concentration of the analyte biomarkers in each sample.

15. The method of claim 1, wherein the biological sample is whole blood, serum, plasma, tissue fluid, cerebrospinal fluid (CSF), synovial fluid, follicular fluid, seminal fluid, amniotic fluid, milk, urine, pleural fluid, ascites, bronchoalveolar lavage, saliva, sputum, tears, perspiration, lymphatic fluid, aspirate, bone marrow aspirate and mucus, or an extract or purification therefrom, or dilution thereof.

16. The method of claim 1, wherein the biological sample is whole blood, serum, or plasma.

17. The method of claim 1, wherein the biological sample is serum or non-activated serum.

\* \* \* \* \*